United States Patent
Morse et al.

(10) Patent No.: US 9,486,545 B2
(45) Date of Patent: Nov. 8, 2016

(54) METHOD OF SCREENING FOR COLON CANCER USING BIOMARKERS

(71) Applicant: H. Lee Moffitt Cancer Center and Research Institute, Inc., Tampa, FL (US)

(72) Inventors: David L. Morse, Tampa, FL (US); Robert J. Gillies, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 261 days.

(21) Appl. No.: 14/041,296

(22) Filed: Sep. 30, 2013

(65) Prior Publication Data

US 2014/0105827 A1    Apr. 17, 2014

Related U.S. Application Data

(63) Continuation of application No. PCT/US2012/031842, filed on Apr. 2, 2012.

(60) Provisional application No. 61/470,200, filed on Mar. 31, 2011.

(51) Int. Cl.
    *G01N 33/574*    (2006.01)
    *C12Q 1/68*      (2006.01)
    *A61K 49/14*     (2006.01)
    *G01N 33/53*     (2006.01)

(52) U.S. Cl.
    CPC ............ *A61K 49/14* (2013.01); *C12Q 1/6886* (2013.01); *G01N 33/57419* (2013.01); *C12Q 2600/158* (2013.01)

(58) Field of Classification Search
    None
    See application file for complete search history.

(56) References Cited

U.S. PATENT DOCUMENTS

2009/0011413 A1*  1/2009  Ishii .................... C12Q 1/6886
                                                       435/6.14

OTHER PUBLICATIONS

Pierce et al., "Optical contrast agents and imaging systems for detection and diagnosis of cancer" 123 International Journal of Cancer 1979-1990 (2008).*
Kan et al., "Diverse somatic mutation patterns and pathway alterations in human cancers" 466 Nature 869-873 (Aug. 12, 2010).*
Joyce et al., "A molecular signature for Epithelial to Mesenchymal transition in a human colon cancer cell system is revealed by large-scale microarray analysis" 26 Clinical and Experimental Metastasis 569-587 (2009).*
Ballestero et al., "Expression of transporters potentially involved in the targeting of cytostatic bile acid derivatives to colon cancer and polyps" 72 Biochemical Pharmacology 729-738 (2006).*
Miwa N, Furuse M, Tsukita S, Niikawa N, Nakamura Y, Furukawa Y. Involvement of claudin-1 in the beta-catenin/Tcf signaling pathway and its frequent upregulation in human colorectal cancers. Oncology research 2001;12:469-476.
Morcos SK, Thomsen HS. Adverse reactions to iodinated contrast media. European Radiology. 2001;11(7):1267-1275.
Morse DL, Balagurunathan Y, Hostetter G, Trissal M, Tafreshi NK, Burke N, et al. Identification of novel pancreatic adenocarcinoma cellsurface targets by gene expression profiling and tissue microarray. Biochem Pharmacol. 2010;80 (5):748-754.
Mrsny RJ, Brown GT, Gerner-Smidt K, Buret AG, Meddings JB, Quan C, et al. A key claudin extracellular loop domain is critical for epithelial barrier integrity. Am J Pathol. 2008;172(4):905-915.
Murphy CJ, Gole AM, Stone JW, Sisco PN, Alkilany AM, Goldsmith EC, et al. Gold Nanoparticles in Biology: Beyond Toxicity to Cellular Imaging. Accounts of Chemical Research. 2008;41(12):1721-1730.
Namasivayam S, Kalra MK, Torres WE, Small WC. Adverse reactions to intravenous iodinated contrast media: an update. Curr Probl Diagn Radiol. 2006;35(4):164-169.
Neal CP, Garcea G, Doucas H, Manson MM, Sutton CD, Dennison AR, et al. Molecular prognostic markers in resectable colorectal liver metastases: a systematic review. Eur J Cancer 2006;42:1728-1743.
Oliveira SS, Morgado-Diaz JA. Claudins: multifunctional players in epithelial tight junctions and their role in cancer. Cellular and molecular life sciences : CMLS 2007;64:17-28.
Oostenbrug LE, Drenth JP, de Jong DJ, Nolte IM, Oosterom E, van Dullemen HM, et al. Association between Toll-like receptor 4 and inflammatory bowel disease. Inflammatory bowel diseases 2005;11:567-575.
Pissuwan D, Cortie CH, Valenzuela SM, Corte MB. Gold nanosphere-antibody conjugates for hyperthermal therapeutic applications. Gold Bulletin. 2007;40(2):121-129.
Ponz de Leon M, Percesepe A. Pathogenesis of colorectal cancer. Digestive and Liver Disease 2000;32:807-821.
Rao J, Dragulescu-Andrasi A, Yao H. Fluorescence imaging in vivo: recent advances. Current opinion in biotechnology 2007;18:17-25.
Rao V, Alleti R, Xu L, Tafreshi NK, Morse DL, Gillies RJ, et al. A sucrose-derived scaffold for multimerization of bioactive peptides. Bioorg Med Chem. 2011;19(21):6474-6482.
Shang L, Fukata M, Thirunarayanan N, Martin AP, Arnaboldi P, Maussang D, et al. Toll-like receptor signaling in small intestinal epithelium promotes B-cell recruitment and IgA production in lamina propria. Gastroenterology 2008;135:529-538.
Shevach EM, Korty PE. Ly-6: a multigene family in search of a function. Immunology today 1989;10:195-200.
Shi H, Xu JM, Hu NZ, Wang XL, Mei Q, Song YL. Transfection of mouse macrophage metalloelastase gene into murine CT-26 colon cancer cells suppresses orthotopic tumor growth, angiogenesis and vascular endothelial growth factor expression. Cancer Lett. 2006;233(1):139-150.

(Continued)

*Primary Examiner* — Nancy J Leith
(74) *Attorney, Agent, or Firm* — Michele L. Lawson; Smith & Hopen, P.A.

(57) ABSTRACT

The present invention relates to biomarkers for colon cancers, specifically adenomas and adenocarcinomas in the GI tract. The inventors have discovered that the expression and/or overexpression of biomarkers such as CLDN1, GPR56, GRM8, LY6G6D, TLR4 and SLCO1B3 are indicative of adenomas and adenocarcinomas. A method of detecting colon cancer using targeted molecular imaging agents is also presented.

27 Claims, 16 Drawing Sheets

(56) References Cited

OTHER PUBLICATIONS

Singh AB, Sharma A, Dhawan P. Claudin family of proteins and cancer: an overview. Journal of oncology 2010;2010:541957, pp. 1-11.

Sulchek TA, Friddle RW, Langry K, Lau EY, Albrecht H, Ratto TV, et al. Dynamic force spectroscopy of parallel individual Mucin1-antibody bonds. Proceedings of the National Academy of Sciences of the United States of America. 2005;102(46):16638-16643.

Takahashi A, Kondoh M, Masuyama A, Fujii M, Mizuguchi H, Horiguchi Y, et al. Role of C-terminal regions of the C-terminal fragment of Clostridium perfringens enterotoxin in its interaction with claudin-4. J Control Release. 2005;108 (1):56-62.

Vagner J, Barany G, Lam KS, Krchnak V, Sepetov NF, Ostrem JA, et al. Enzyme-mediated spatial segregation on individual polymeric support beads: application to generation and screening of encoded combinatorial libraries. Proc Natl Acad Sci U S A. 1996;93(16):8194-8199.

Vagner J, Xu L, Handl HL, Josan JS, Morse DL, Mash EA, et al. Heterobivalent ligands crosslink multiple cell-surface receptors: the human melanocortin-4 and delta-opioid receptors. Angew Chem Int Ed Engl. 2008;47(9):1685-1688.

van Dam Gm, Themelis G, Crane LM, Harlaar NJ, Pleijhuis RG, Kelder W, et al. Intraoperative tumor-specific fluorescence imaging in ovarian cancer by folate receptor-alpha targeting: first in-human results. Nature medicine 2011;17:1315-1319.

Wang S, Fan W, Kim G, Hah HJ, Lee YE, Kopelman R, et al. Novel methods to incorporate photosensitizers into nanocarriers for cancer treatment by photodynamic therapy. Lasers in surgery and medicine 2011;43:686-695.

Wang TD. Targeted imaging of flat and depressed colonic neoplasms. Gastrointestinal endoscopy clinics of North America 2010;20:579-583.

Wang X, Peng L, Liu R, Gill SS, Lam KS. Partial alloc-deprotection approach for ladder synthesis of "onebead one-compound" combinatorial libraries. J Comb Chem. 2005;7(2):197-209.

Wang X, Tully O, Ngo B, Zitin M, Mullin JM. Epithelial tight junctional changes in colorectal cancer tissues. TheScientificWorldJournal 2011;11:826-841.

Williams AF. Emergence of the Ly-6 superfamily of GPI-anchored molecules. Cell biology international reports 1991;15:769-777.

Williams PM. Analytical descriptions of dynamic force spectroscopy: behaviour of multiple connections. Analytica Chimica Acta. 2003;479(1):107-115.

Xu L, Vagner J, Josan J, Lynch RM, Morse DL, Baggett B, et al. Enhanced targeting with heterobivalent ligands. Mol Cancer Ther. 2009;8(8):2356-2365.

International Search Report for PCT/US2012/031842, International filing date Apr. 2, 2012, and a mailing date of Oct. 29, 2012.

Yamada M, Ichikawa T, li M, Sunamoto M, Itoh K, Tamura N, et al. Discovery of novel and potent small-molecule inhibitors of NO and cytokine production as antisepsis agents: synthesis and biological activity of alkyl 6-(N-substituted sulfamoyl)cyclohex-1-ene-1-carboxylate. J Med Chem. 2005;48(23):7457-7467.

Yamamoto T, Nair P, Jacobsen NE, Vagner J, Kulkarni V, Davis P, et al. Improving metabolic stability by glycosylation: bifunctional peptide derivatives that are opioid receptor agonists and neurokinin 1 receptor antagonists. J Med Chem. 2009;52(16):5164-5175.

Yamamoto T, Nair P, Ma SW, Davis P, Yamamura HI, Vanderah TW, et al. The biological activity and metabolic stability of peptidic bifunctional compounds that are opioid receptor agonists and neurokinin-1 receptor antagonists with a cystine moiety. Bioorg Med Chem. 2009;17(20):7337-7343.

Yamamoto T, Nair P, Vagner J, Largent-Milnes T, Davis P, Ma SW, et al. A structure-activity relationship study and combinatorial synthetic approach of C-terminal modified bifunctional peptides that are delta/mu opioid receptor agonists and neurokinin 1 receptor antagonists. J Med Chem. 2008;51(5):1369-1376.

Ying J, Gu X, Cai M, Dedek M, Vagner J, Trivedi DB, et al. Design, synthesis, and biological evaluation of new cyclic melanotropin peptide analogues selective for the human melanocortin-4 receptor. J Med Chem. 2006;49 (23):6888-6896.

Young MR, Ileva LV, Bernardo M, Riffle LA, Jones YL, Kim YS, et al. Monitoring of tumor promotion and progression in a mouse model of inflammation-induced colon cancer with magnetic resonance colonography. Neoplasia. 2009;11 (3):237-246.

Abdelzaher E, Rizk AM, Bessa SS, Omer KM. Predictive value of immunohistochemical expression of claudin-1 in colonic carcinoma. Journal of the Egyptian National Cancer Institute 2011;23:123-131.

Barkey NM, Tafreshi NK, Josan JS, De Silva CR, Sill KN, Hruby VJ, et al. Development of Melanoma-Targeted Polymer Micelles by Conjugation of a Melanocortin 1 Receptor (MC1R) Specific Ligand. J Med Chem. 2011;54 (23):8078-8084.

Bevan DE, Martinko AJ, Loram LC, Stahl JA, Taylor FR, Joshee S, et al. Selection, Preparation, and Evaluation of Small- Molecule Inhibitors of Toll-Like Receptor 4. ACS Med Chem Lett. 2010;1(5):194-198.

Bipat S, Glas AS, Slors FJM, Zwinderman AH, Bossuyt PMM, Stoker J. Rectal cancer: Local staging and assessment of lymph node involvement with endoluminal US, CT, and MR imaging—A meta-analysis. Radiology. 2004;232 (3):773-783.

Bipat S, Niekel MC, Comans EF, Nio CY, Bemelman WA, Verhoef C, et al. Imaging modalities for the staging of patients with colorectal cancer. The Netherlands journal of medicine 2012;70:26-34.

Boisselier E, Astruc D. Gold nanoparticles in nanomedicine: preparations, imaging, diagnostics, therapies and toxicity. Chemical Society Reviews. 2009;38(6):1759-1782.

Boitano S, Flynn AN, Schulz SM, Hoffman J, Price TJ, Vagner J. Potent agonists of the protease activated receptor 2 (PAR2). J Med Chem. 2011;54(5):1308-1313.

Bosman FT. Prognostic value of pathological characteristics ofcolorectal cancer. Eur J Cancer 1995;31A:1216-1221.

Brabez N, Lynch RM, Xu L, Gillies RJ, Chassaing G, Lavielle S, et al. Design, synthesis, and biological studies of efficient multivalent melanotropin ligands: tools toward melanoma diagnosis and treatment. J Med Chem. 2011;54 (20):7375-7384.

Cairo CW, Gestwicki JE, Kanai M, Kiessling LL. Control of multivalent interactions by binding epitope density. Journal of the American Chemical Society. 2002;124(8):1615-1619.

Calvanese V, Mallya M, Campbell RD, Aguado B. Regulation of expression of two LY-6 family genes by intron retention and transcription induced chimerism. BMC molecular biology 2008;9:81, pp. 1-17.

Cammarota R, Bertolini V, Pennesi G, Bucci EO, Gottardi O, Garlanda C, et al. The tumor microenvironment of colorectal cancer: stromal TLR-4 expression as a potential prognostic marker. J Transl Med. 2010;8:112, pp. 1-16.

Cario E, Podolsky DK. Differential alteration in intestinal epithelial cell expression of toll-like receptor 3 (TLR3) and TLR4 in inflammatory bowel disease. Infection and immunity 2000;68:7010-7017.

Chavez SA, Martinko AJ, Lau C, Pham MN, Cheng K, Bevan DE, et al. Development of betaamino alcohol derivatives that inhibit Toll-like receptor 4 mediated inflammatory response as potential antiseptics. J Med Chem. 2011;54 (13):4659-4669.

Chen Y, Chang KJ, Hwang LH, Chen CN, Tseng SH. Establishment and characterization of a rectal cancer model in mice: application to cytokine gene therapy. Int J Colorectal Dis. 2002;17(6):388-395.

Chen YS, Hung YC, Liau I, Huang GS. Assessment of the In Vivo Toxicity of Gold Nanoparticles. Nanoscale Research Letters. 2009;4(8):858-864.

de Oliveira SS, de Oliveira IM, De Souza W, Morgado-Diaz JA. Claudins upregulation in human colorectal cancer. FEBS letters 2005;579:6179-6185.

Deli MA. Potential use of tight junction modulators to reversibly open membranous barriers and improve drug delivery. Biochim Biophys Acta. 2009;1788(4):892-910.

Eck W, Craig G, Sigdel A, Ritter G, Old LJ, Tang L, et al. PEGylated Gold Nanoparticles Conjugated to Monoclonal F19 Antibodies as Targeted Labeling Agents for Human Pancreatic Carcinoma Tissue. Acs Nano. 2008;2 (11):2263-2272.

(56) References Cited

OTHER PUBLICATIONS

Einerhand AW, Renes IB, Makkink MK, van der Sluis M, Buller HA, Dekker J. Role of mucins in inflammatory bowel disease: important lessons from experimental models. European journal of gastroenterology & hepatology 2002;14:757-765.
Fearon ER, Vogelstein B. A genetic model for colorectal tumorigenesis. Cell 1990;61:759-767.
Finlay GJ. Genetics, molecular biology and colorectal cancer. Mutation research 1993;290:3-12.
Flynn AN, Tillu DV, Asiedu MN, Hoffman J, Vagner J, Price TJ, et al. The protease-activated receptor-2-specific agonists 2-aminothiazol-4-yl-LIGRL-NH2 and 6-aminonicotinyl-LIGRL-NH2 stimulate multiple signaling pathways to induce physiological responses in vitro and in vivo. J Biol Chem. 2011;286(21):19076-19088.
McGinty J, Galletly NP, Dunsby C, Munro I, Elson DS, Requejo-Isidro J, et al. Wide-field fluorescence lifetime imaging of cancer. Biomedical optics express 2010;1:627-640.
Grassetto G, Capirci C, Marzola MC, Rampin L, Chondrogiannis S, Musto A, et al. Colorectal cancer: prognostic role of (18)FFDG-ET/CT. Abdominal Imaging 2012, 37:575-579.
Grone J, Weber B, Staub E, Heinze M, Klaman I, Pilarsky C, et al. Differential expression of genes encoding tight junction proteins in colorectal cancer: frequent dysregulation of claudin-1, -8 and -12. International journal of colorectal disease 2007;22:651-659.
Gupta A, Wang S, Pera P, Rao KV, Patel N, Ohulchanskyy TY, et al. Multifunctional nanoplatforms for fluorescence imaging and photodynamic therapy developed by post-loading photosensitizer and fluorophore to polyacrylamide nanoparticles. Nanomedicine 2012, 8(6): 941-950.
Hainfeld JF, O'Connor MJ, Dilmanian FA, Slatkin DN, Adams DJ, Smilowitz HM. Micro-CT enables microlocalisation and quantification of Her2-targeted gold nanoparticles within tumour regions. Br J Radiol. 2011;84(1002):526-533.
He X, Wang K, Cheng Z. In vivo near-infrared fluorescence imaging of cancer with nanoparticle-based probes. Wiley interdisciplinary reviews Nanomedicine and nanobiotechnology 2010;2:349-366.
Hruby VJ, Balse PM. Conformational and topographical considerations in designing agonist peptidomimetics from peptide leads. Curr Med Chem. 2000;7(9):945-970.
Hruby VJ, Qui W, Okayama T, Soloshonok VA. Design of nonpeptides from peptide ligands for peptide receptors. Methods Enzymol. 2002;343:91-123.
Hruby VJ. Designing peptide receptor agonists and antagonists. Nat Rev Drug Discov. 2002;1(11):847-858.
Huang XH, Jain PK, Ei-Sayed IH, EI-Sayed MA. Gold nanoparticles: interesting optical properties and recent applications in cancer diagnostic and therapy. Nanomedicine. 2007;2(5):681-693.
Iftimia N, Iyer AK, Hammer DX, Lue N, Mujat M, Pitman M, et al. Fluorescence-guided optical coherence tomography imaging for colon cancer screening: a preliminary mouse study. Biomedical optics express 2012;3:178-191.
Ii M, Matsunaga N, Hazeki K, Nakamura K, Takashima K, Seya T, et al. A novel cyclohexene derivative, ethyl (6R)-6-[N-(2-Chloro-4-fluorophenyl)sulfamoyl]cyclohex-1-ene-1-carboxylate (TAK-242), selectively inhibits toll-like receptor 4-mediated cytokine production through suppression of intracellular signaling. Mol Pharmac 2006;69(4):1288-1295.
Itzkowitz SH, Yio X. Inflammation and cancer IV. Colorectal cancer in inflammatory bowel disease: the role of inflammation. American journal of physiology Gastrointestinal and liver physiology 2004;287:G7-17.
Jackson PA, Abd Rahman WNW, Wong CJ, Ackerly T, Geso M. Potential dependent superiority of gold nanoparticles in comparison to iodinated contrast agents. European Journal of Radiology. 2010;75(1):104-109.
Josan JS, Morse DL, Xu L, Trissal M, Baggett B, Davis P, et al. Solid-phase synthetic strategy and bioevaluation of a labeled delta-opioid receptor ligand Dmt-Tic-Lys for in vivo imaging. Org Lett. 2009;11(12):2479-2482.
Klessen C, Rogalla P, Taupitz M. Local staging of rectal cancer: the current role of MRI. European Radiology. 2007;17 (2):379-389.
Krause G, Winkler L, Mueller SL, Haseloff RF, Piontek J, Blasig IE. Structure and function of claudins. Biochim Biophys Acta. 2008;1778(3):631-645.
Lal-Nag M, Morin PJ. Protein family review, The claudins. Genome biology 2009;10:235.1-235.7.
Lam KS, Salmon SE, Hersh EM, Hruby VJ, Kazmierski WM, Knapp RJ. A new type of synthetic peptide library for identifying ligand-binding activity. Nature 1991;354(6348):82-84.
Lang EK, Foreman J, Schlegel JU, Leslie C, List A, Mccormick P. The Incidence of Contrast-Medium Induced Acute Tubular-Necrosis Following Arteriography—a Preliminary-Report. Radiology. 1981;138(1):203-206.
Liu R, Marik J, Lam KS. Design, synthesis, screening, and decoding of encoded one-bead one-compound peptidomimetic and small molecule combinatorial libraries. Methods Enzymol. 2003;369:271-287.
Mallya M, Campbell RD, Aguado B. Transcriptional analysis of a novel cluster of LY-6 family members in the human and mouse major histocompatibility complex: five genes with many splice forms. Genomics 2002;80:113-123.
Mammen M, Choi SK, Whitesides GM. Polyvalent interactions in biological systems: Implications for design and use of multivalent ligands and inhibitors. Angewandte Chemie-International Edition. 1998;37(20):2755-2794.
Martin TA, Jiang WG. Loss of tight junction barrier function and its role in cancer metastasis. Biochimica et biophysica acta 2009;1788:872-891.
Masuyama A, Kondoh M, Seguchi H, Takahashi A, Harada M, Fujii M, et al. Role of N-terminal amino acids in the absorption-enhancing effects of the c-terminal fragment of Clostridium perfringens enterotoxin. J Pharmacol Exp Ther. 2005;314(2):789-795.
Mayorov AV, Cai M, Palmer ES, Dedek MM, Cain JP, Van Scoy AR, et al. Structure-activity relationships of cyclic lactam analogues of alpha-melanocyte-stimulating hormone (alpha-MSH) targeting the human melanocortin-3 receptor. J Med Chem. 2008;51(2):187-195.

* cited by examiner

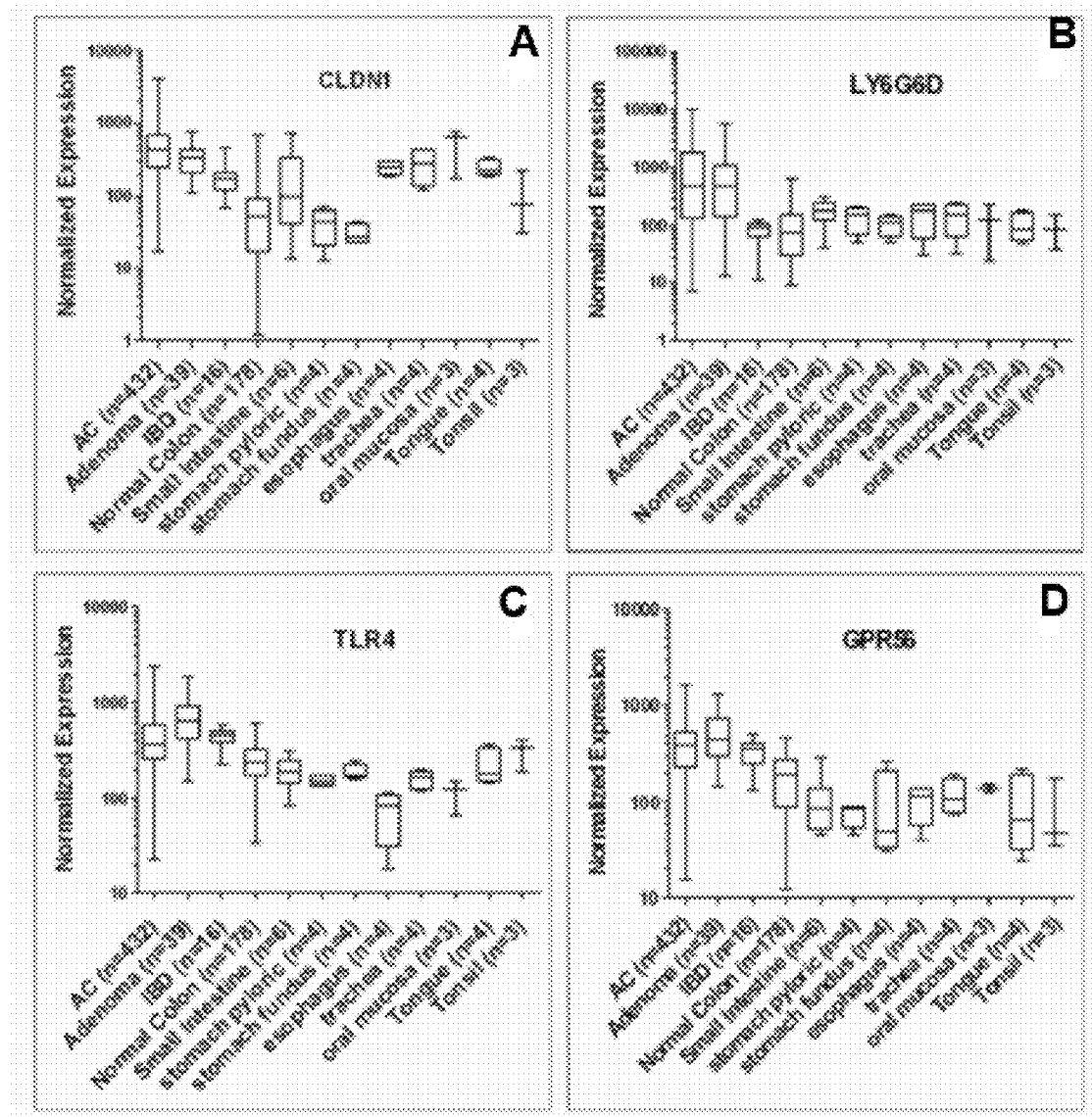
FIG. 2A-D

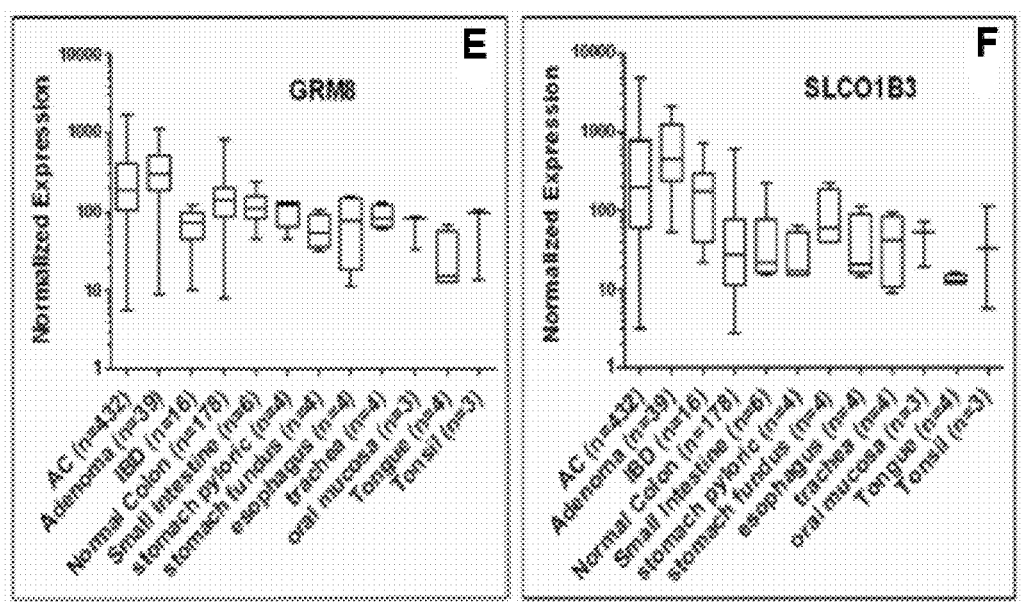
FIG. 2E-F

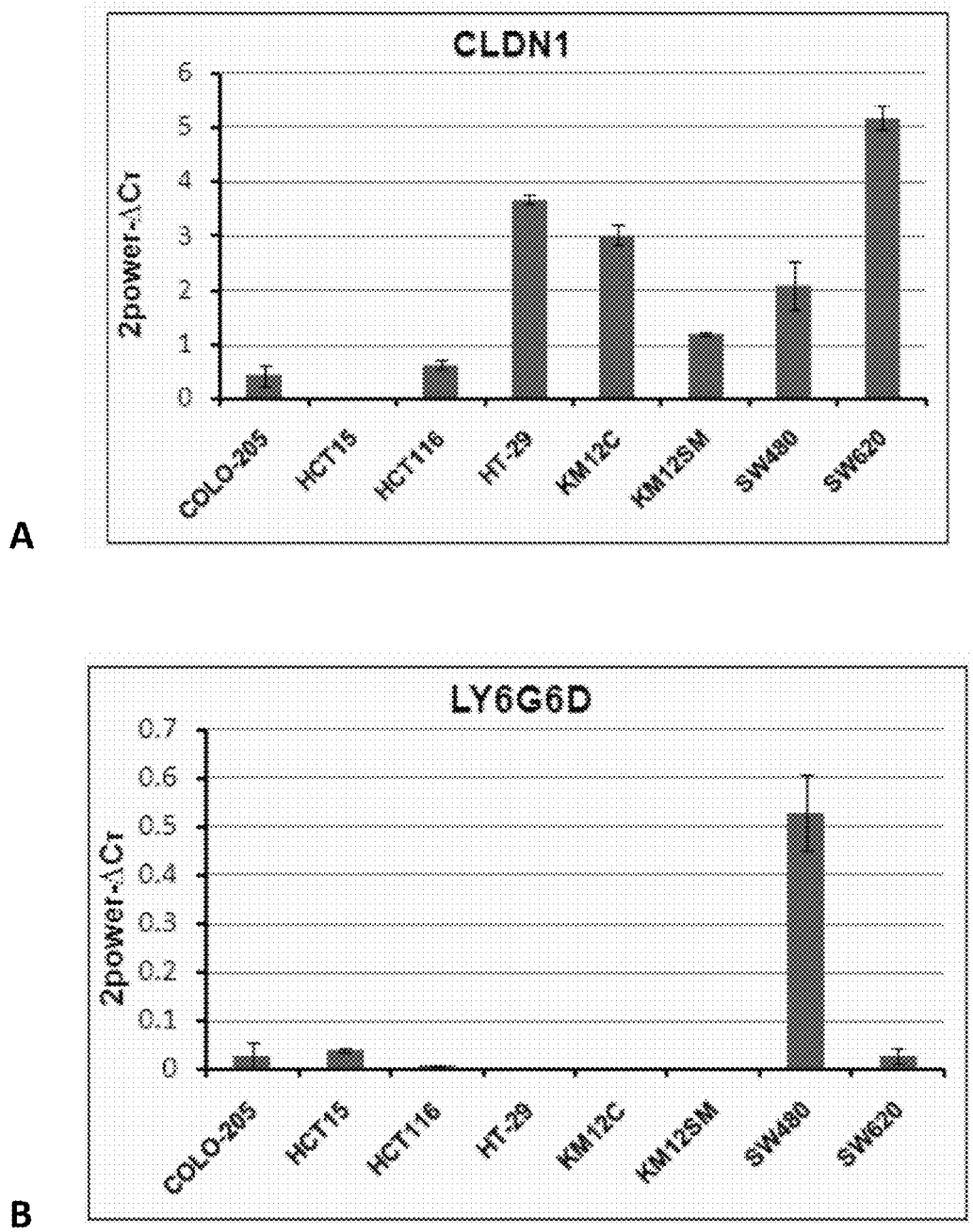
FIG. 6A-B

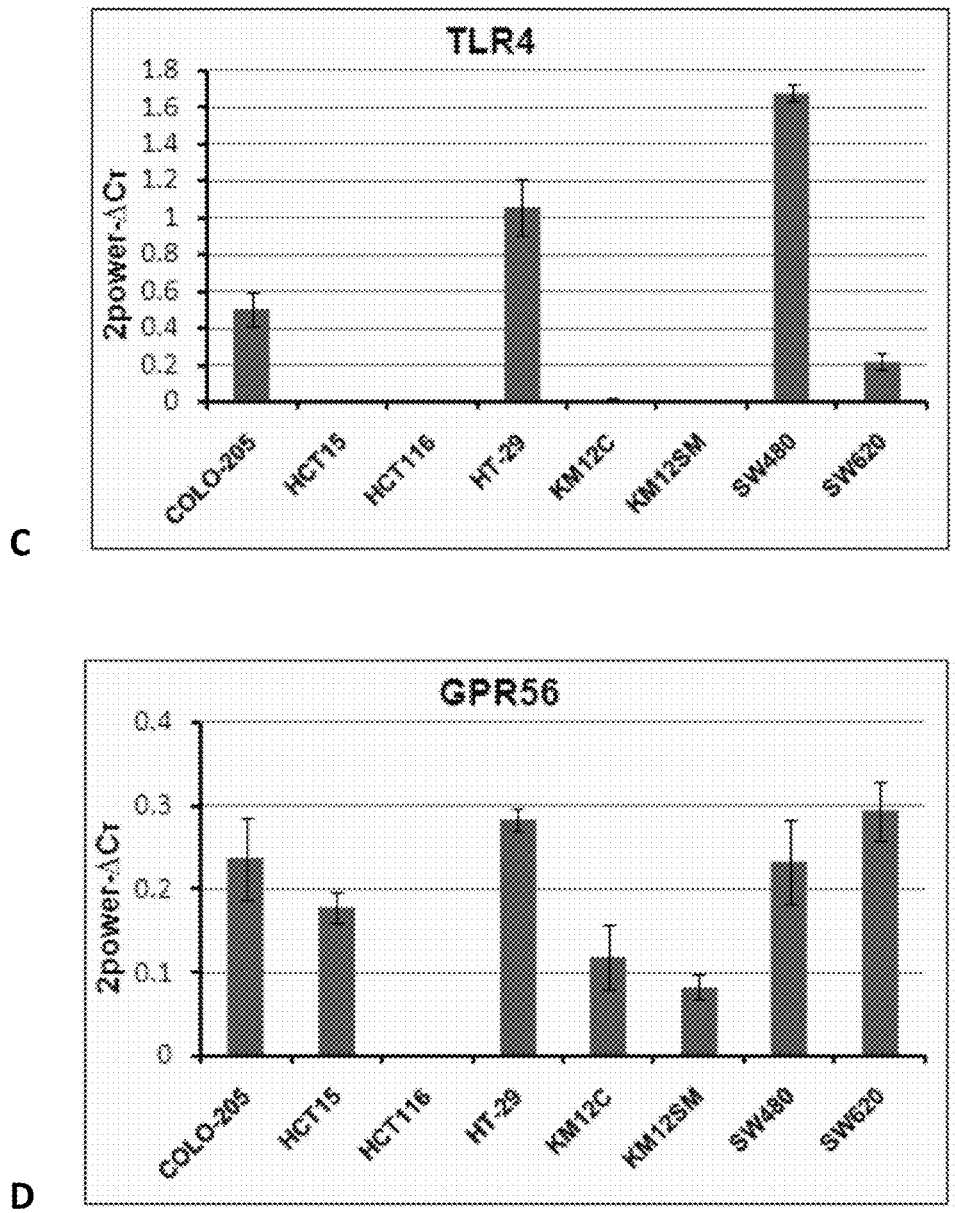
FIG. 6C-D

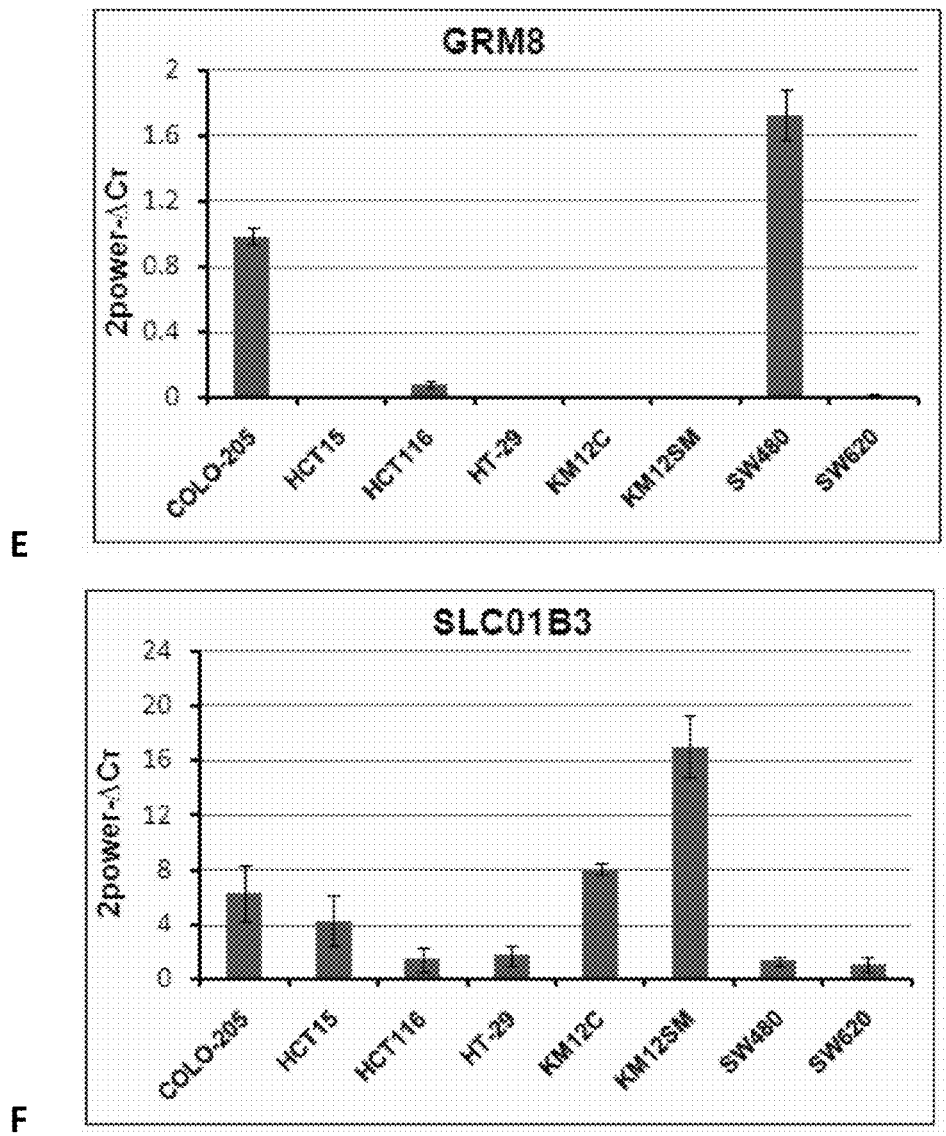
FIG. 6E-F

FIG. 10A-E

```
SEQUENCE LISTING

<160> NUMBER OF SEQ ID NOS: 12

<210> SEQ ID NO 1
<211> LENGTH: 22
<212> TYPE: DNA
<213> ORGANISM: artificial sequence
<220> FEATURE:
<223> OTHER INFORMATION: Forward primer for TLR4

<400> SEQUENCE: 1
tggccattgc tgccaacatc at                                            22

<210> SEQ ID NO 2
<211> LENGTH: 22
<212> TYPE: DNA
<213> ORGANISM: artificial sequence
<220> FEATURE:
<223> OTHER INFORMATION: Reverse primer for TLR4

<400> SEQUENCE: 2
tcaaagatac accagcggct ct                                            22

<210> SEQ ID NO 3
<211> LENGTH: 22
<212> TYPE: DNA
<213> ORGANISM: artificial sequence
<220> FEATURE:
<223> OTHER INFORMATION: Forward primer for GPR56

<400> SEQUENCE: 3
agttctgggc ctttggcatt ca                                            22
```

<210> SEQ ID NO 4
<211> LENGTH: 22
<212> TYPE: DNA
<213> ORGANISM: artificial sequence
<220> FEATURE:
<223> OTHER INFORMATION: Reverse primer for GPR56

<400> SEQUENCE: 4
agcacaatgc aaggcacaca gt                                           22

<210> SEQ ID NO 5
<211> LENGTH: 22
<212> TYPE: DNA
<213> ORGANISM: artificial sequence
<220> FEATURE:
<223> OTHER INFORMATION: Forward primer for GRM8

<400> SEQUENCE: 5
tgtgtttcag ctatgcagcc ct                                           22

<210> SEQ ID NO 6
<211> LENGTH: 22
<212> TYPE: DNA
<213> ORGANISM: artificial sequence
<220> FEATURE:
<223> OTHER INFORMATION: Reverse primer for GRM8

<400> SEQUENCE: 6
acttgggcgc tgtgacagat tt                                           22

<210> SEQ ID NO 7
<211> LENGTH: 21
<212> TYPE: DNA
<213> ORGANISM: artificial sequence
<220> FEATURE:
<223> OTHER INFORMATION: Forward primer for CLDN1

<400> SEQUENCE: 7
tggaaagggt gttggcattg g                                            21

<210> SEQ ID NO 8
<211> LENGTH: 21
<212> TYPE: DNA
<213> ORGANISM: artificial sequence
<220> FEATURE:
<223> OTHER INFORMATION: Reverse primer for CLDN1

<400> SEQUENCE: 8
gcagccaaat gccttgctca a                                            21

<210> SEQ ID NO 9
<211> LENGTH: 22
<212> TYPE: DNA
<213> ORGANISM: artificial sequence
<220> FEATURE:
<223> OTHER INFORMATION: Forward primer for SLCO1B3

<400> SEQUENCE: 9
ttggctttgc actgggatct ct                                           22

<210> SEQ ID NO 10
<211> LENGTH: 21
<212> TYPE: DNA
<213> ORGANISM: artificial sequence
<220> FEATURE:
<223> OTHER INFORMATION: Reverse primer for SLCO1B3

```
<400> SEQUENCE: 10
aaccaagcca ccaagctcca a                                          21

<210> SEQ ID NO 11
<211> LENGTH: 20
<212> TYPE: DNA
<213> ORGANISM: artificial sequence
<220> FEATURE:
<223> OTHER INFORMATION: Forward primer for LY6G6D

<400> SEQUENCE: 11
atcttgctca gctccctgct                                            20

<210> SEQ ID NO 12
<211> LENGTH: 22
<212> TYPE: DNA
<213> ORGANISM: artificial sequence
<220> FEATURE:
<223> OTHER INFORMATION: Reverse primer for LY6G6D

<400> SEQUENCE: 12
tcacggcctc tttgcaagaa ct                                         22
```

METHOD OF SCREENING FOR COLON CANCER USING BIOMARKERS

CROSS REFERENCE TO RELATED APPLICATIONS

This application is a continuation of prior filed International Application, Serial Number PCT/US2012/031842 filed Apr. 2, 2012, which claims priority to U.S. Provisional Application No. 61/470,200 entitled "Identification and Validation of Surrogate Markers for Colon Adenoma and Adenocarcinoma", filed Mar. 31, 2011, the contents of which are hereby incorporated by reference into this disclosure.

FIELD OF THE INVENTION

This invention relates to detection and diagnosis of dysplastic and early neoplastic colonic lesions. More specifically, it relates to targeted molecular imaging agents for the early detection of colon cancer via targeted and potentially prepless colonography using CT or MRI contrast.

BACKGROUND OF THE INVENTION

Colorectal cancer (CRC) is third leading cause of the morbidity and mortality for both men and women in well-developed and industrialized countries like United States and United Kingdom. (Ponz de Leon M, Percesepe A. Pathogenesis of colorectal cancer. Digestive and Liver Disease 2000; 32:807-21). In the United States alone, it is the third most common neoplasm incurring health care costs estimated at $8 billion. Approximately 75% of CRCs are sporadic and occur in average-risk individuals without a familial predisposition.

Colon cancer arises from the pre-existing adenomatous polyps which are dysplastic or neoplastic lesions at an early stage. Colon cancer is treatable is detected early and survival is improved by early diagnosis. Hence, screening for CRC is recommended for persons≥50 years of age. Patients diagnosed with advanced CRC typically die within 5 years. Without screening, CRC is typically detected as adenocarcinoma at an advanced stage, where treatments are less effective.

Currently available screening techniques include: (1) fecal occult blood testing (FOBT) which detects only 30-40% of CRC and 10% of adenomas; (2) sigmoidoscopy fails to detect lesions in the proximal colon which represents 40% of all colorectal cancers, misses 10-15% of sigmoid colon carcinomas, and is uncomfortable for patients; (3) double contrast barium enema (DCBE), which visualizes the entire colon but has only 44% sensitivity for detection of polyps >1 cm in diameter, is highly operator-dependent, and is uncomfortable for the patient; and (4) colonoscopy which is the current standard of care, but has a significant miss rate of 24% for adenomas overall, 27% of adenomas <5 mm, 13% of adenomas 6-9 mm, and 6% of adenomas >1 cm. Colonoscopy also fails to reach the caecum of 5-10% of average risk patients. (Fenlon H M. Virtual colonoscopy. The British journal of surgery 2002; 89:1-3). Failure rates for colonoscopy, barium enema and flexible sigmoidoscopy are 9%, 20% and 50% respectively. (Frenette C, Strum W. Relative Rates of Missed Diagnosis for Colonoscopy, Barium Enema, and Flexible Sigmoidoscopy in 379 Patients with Colorectal Cancer. Journal of Gastrointestinal Cancer 2007; 38:148-53). Possibly of greater importance, colonoscopy has a problem of low patient compliance, which may be due the requirement of a cathartic bowel preparation, general anesthesia, cost and the invasiveness of the procedure.

In addition to colonoscopy, an emerging, less invasive method is Virtual Colonoscopy (VC) wherein multi-slice computed tomography (CT-VC) and magnetic resonance imaging (MRI-VC) images are analyzed for the presence of visible (>0.5 cm) polyps. Although VC methods require bowel preparation and distention of the bowel by insufflation of the bowel, these image acquisitions are short in duration relative to the length of the colonoscopy procedure and do not require anesthesia thus VC procedures tend to be lower in cost. The entire colon is visualized, allowing for accurate and sensitive lesion detection. However, specificity of detection for these methods is lower than colonoscopy. As with colonoscopy, an inadequate bowel preparation can lead to false positives. Hence, currently available screening methods for CRC suffer from low patient compliance, high cost and inadequate specificity and sensitivity of detection due to the colon's complicated physiology and inadequate bowel preparation. (Edwards C. Physiology of the colorectal barrier. Advanced Drug Delivery Reviews 1997; 28:173-90)

The genetic model of colorectal carcinogenesis developed by Vogelstein et al. has shown that there is an accumulation of a series of molecular genetic abnormalities over time that determines the neoplastic phenotype of CRC. (Fearon E R, Vogelstein B. A genetic model for colorectal tumorigenesis. Cell 1990; 61:759-67; Finlay G J. Genetics, molecular biology and colorectal cancer. Mutation research 1993; 290:3-12). In the last 2-3 decades, we have greatly improved our understanding of tumor biology, molecular pathways, and the hereditary and environmental factors that lead to colon carcinogenesis. Based on the molecular profile of colon tumors, there is an opportunity to develop targeted diagnostic methods with potential for use in personalized patient care. (Neal C P, Garcea G, Doucas H, Manson M M, Sutton C D, Dennison A R, et al. Molecular prognostic markers in resectable colorectal liver metastases: a systematic review. Eur J Cancer 2006; 42:1728-43; Bosman F T. Prognostic value of pathological characteristics of colorectal cancer. Eur J Cancer 1995; 31A:1216-21). The discovery of molecular markers that are expressed on the tumor cell-surface may lead to the development of targeted molecular imaging and therapeutic agents for CRC.

For the early detection and prognostic prediction of colon cancer, the screening methods available have not that specificity and sensitivity because of colon's complicated physiology and cleaning process. (Edwards C. Physiology of the colorectal barrier. Advanced Drug Delivery Reviews 1997; 28:173-90). For this reason, what is needed is an alternative screening/detection approach that is able to reliably and accurately detect colon cancer in its earliest stages.

SUMMARY OF THE INVENTION

The inventors have discovered markers that are highly expressed on the CRC tumor cell surface, but are not expressed, or are expressed relatively low on the surrounding unaffected colon tissue. These CRC specific markers can be used to develop targeted molecular imaging probes that specifically deliver CT or MRI contrast agents to colon adenomas and adenocarcinomas but otherwise clear from the surrounding tissue. These agents can greatly improve the specificity and sensitivity of detection for both VC methods.

For specific targeting, ligands are attached to the contrast agents that bind to target markers expressed on the cell-surface of colon adenoma and adenocarcinoma, but are not expressed in unaffected colon and other tissues in the gastrointestinal tract. By expression profiling of DNA microarray data from patient samples, the inventors have identified >10 markers that are highly and broadly expressed among patient adenoma and adenocarcinoma samples while having low or no expression in unaffected GI tissues. As few as two of these markers (TLR4 and CLDN1) generate 100% coverage as determined by mRNA expression (n=308). By immunohistochemistry (IHC), the inventors confirmed high protein expression of CLDN1, LY6G6D and TLR4 in CRC, and high expression of at least one of these markers was observed in 97% of the samples.

In practical use, a patient would drink a cocktail of targeted contrast agents that cover 100% of CRCs, as described herein, and be imaged 2-3 days later without the need for bowel prep. These specific and selective contrast agents target both luminal and flat adenomatous lesions for detection with high conspicuity. This approach is designed to improve sensitivity, specificity, compliance and the cost-benefit of this important screening test. These specific contrast agents can be used to improve the detection of lesions for removal during traditional colonoscopy.

In an embodiment, a method of screening for colon cancer is presented comprising: obtaining a gastrointestinal tract sample suspected of containing a neoplasm from a patient; and assaying the sample for the presence of at least one biomarker wherein the biomarker is selected from the group consisting of CLDN1, GPR56, GRM8, LY6G6D, TLR4 and SLCO1B3 wherein the presence of the at least one biomarker is indicative of colon cancer.

The biomarker can be in combinations such as the combination of CLDN1, LY6G6D and TLR4; TLR4, GPR56 and CLDN1; or TLR4 and GRM8. Alternatively, the biomarker can be singular such as CLDN1 or TLR4.

In another embodiment, a method of screening for colon cancer is presented comprising: obtaining an expression level of at least one biomarker wherein the biomarker is selected from the group consisting of CLDN1, GPR56, GRM8, LY6G6D, TLR4 and SLCO1B3 in a patient sample; and comparing the expression level of the at least one biomarker to a predetermined control level wherein an increase in the expression level of the at least one biomarker as compared to the predetermined control level indicates the presence of neoplasia.

The biomarker can be in combinations such as the combination of CLDN1, LY6G6D and TLR4; TLR4, GPR56 and CLDN1; or TLR4 and GRM8. Alternatively, the biomarker can be singular such as CLDN1 or TLR4.

In a further embodiment, a method of screening for colon cancer is presented comprising: providing at least one contrast agent; binding the at least one contrast agent to at least one biomarker-specific synthetic ligand wherein the biomarker is selected from the group consisting of CLDN1, GPR56, GRM8, LY6G6D, TLR4 and SLCO1B3; adding the contrast agent with bound ligand to a pharmaceutically acceptable carrier to form a composition; administering the composition to a patient; and imaging the patient using radiation at least about 8.5 hours after administration wherein detection of the contrast agent with bound ligand in the patient is indicative of colon cancer.

Multivalent binding may be used to bind multiple copies of the biomarker-specific ligand to the contrast agent.

The biomarker can be in combinations such as the combination of CLDN1, LY6G6D and TLR4; TLR4, GPR56 and CLDN1; or TLR4 and GRM8. Alternatively, the biomarker can be singular such as CLDN1 or TLR4.

The patient may be imaged using magnetic resonance imaging (MRI) or computed tomography (CT).

The contrast agent may be a magnetic resonance imaging (MRI) contrast agent that is a Gd-sucrose construct. The Gd-sucrose construct may be comprised of a sucrose scaffold conjugated with a plurality of Gd(III)-DOTA chelates. The number of chelates may be between about 6 and about 8.

The contrast agent may a computed tomography (CT) contrast agent that is a plurality of gold nanoparticles.

BRIEF DESCRIPTION OF THE DRAWINGS

For a fuller understanding of the invention, reference should be made to the following detailed description, taken in connection with the accompanying drawings, in which:

FIG. 2A-F are a series of images of DNA microexpression profiles of CRC cell-surface markers. Values are presented as a box plot using logio scale. (A) CLDN1; (B) LY6G6D; (C) TLR4; (D) GPR56; (E) GRM8; (F) SLCO1B3.

FIG. 6A-F are a series of images illustrating the qRT-PCR results for marker expression in human colorectal cancer cell lines. The markers examined include: (A) CLDN1, (B) LY6G6D, (C) TLR4, (D) GPR56, (E) GRM8 and (F) SLCO1B3.

DETAILED DESCRIPTION OF THE PREFERRED EMBODIMENT

Figure 1:
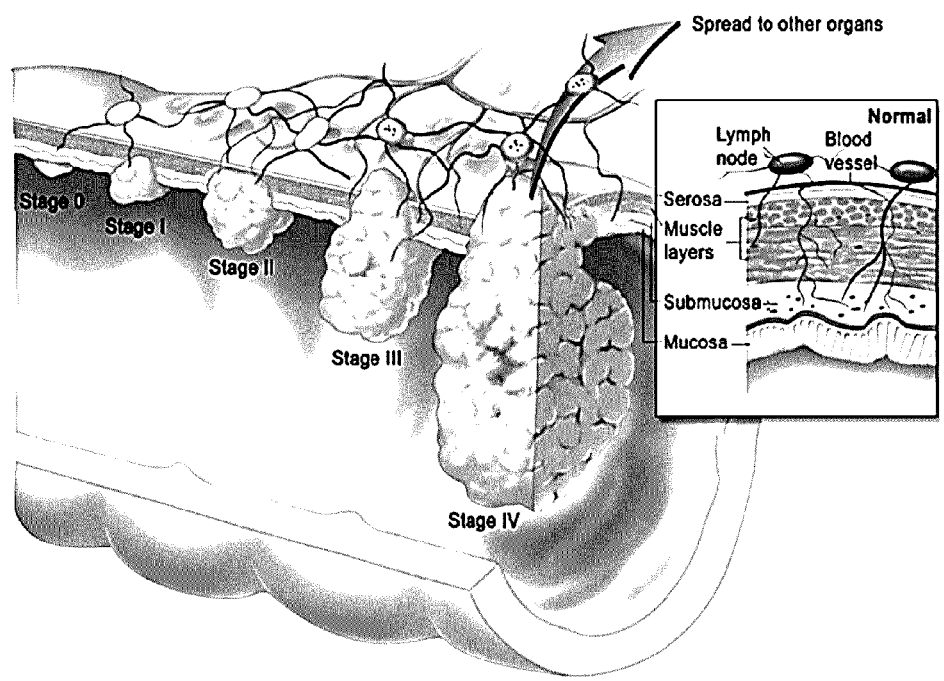
FIG. 1 is an image of the colon. The colon is about 3 in. (8 cm) in diameter and about 5 ft. (1.7 m) long. The various stages of colon cancer are as follows: Stage 1—Cells that line the colon are very active, constantly dividing and creating buds, known as polyps. Most polyps are small, benign growths that eventually stop growing. Stage 2—a tiny percentage of these polyps keep growing, sometimes for 10 years or more. Various genetic mutations can transform them into cancerous tumors. Stage 3—As these tumors grow larger, they gather more mutations and begin to burrow deeper and deeper into the muscle wall that surrounds the colon. Stage 4—Once the cancer invades the blood and lymph systems, malignant cells can break off and spread to other organs, such as the liver, lungs and stomach.

In the following detailed description of the preferred embodiments, reference is made to the accompanying drawings, which form a part hereof, and within which are shown by way of illustration specific embodiments by which the invention may be practiced. It is to be understood that other embodiments by which the invention may be practiced. It is to be understood that other embodiments may be utilized and structural changes may be made without departing from the scope of the invention.

Definitions

As used in the specification and claims, the singular form "a", "an" and "the" include plural references unless the context clearly dictates otherwise. For example, the term "a nanoparticle" includes a plurality of nanoparticles, including mixtures thereof.

Concentrations, amounts, solubilities, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1 to about 5" should be interpreted to include not only the explicitly recited values of about 1 to about 5, but also include the individual values and sub-ranges within the indicated range, to the tenth of the unit. Thus, included in this numerical range are individual values such as 2, 3, and 4 and sub-ranges such as from 1-3, from 2-4 and from 3-5, etc. This same principle applies to ranges reciting only one numerical value. Furthermore, such an interpretation should apply regardless of the range or the characteristics being described.

All numerical designations, such as pH, temperature, time, concentration, and molecular weight, including ranges, are approximations which are varied up or down by increments of 1.0 or 0.1, as appropriate. It is to be understood, even if it is not always explicitly stated that all numerical designations are preceded by the term "about". It is also to be understood, even if it is not always explicitly stated, that the reagents described herein are merely exemplary and that equivalents of such are known in the art and can be substituted for the reagents explicitly stated herein.

"Subject" is used to describe an animal, preferably a human, to whom treatment is administered, including prophylactic treatment with the compositions of the present invention. "Subject" and "patient" are used interchangeably herein.

The proteins of the present invention can serve as biomarkers for the diagnosis of disease in which the presence of the specific protein on the cell surface may be indicative of the presence of disease. Alternatively, the level of the specific protein can be compared to a baseline or control level in which if the level is above the control level, a certain disease is implicated.

The terms "diagnosing" or "diagnosis" as used herein refers to the determination of whether a subject comprises a disease or condition such as cancer. "Diagnosis" and "diagnosing" is used interchangeably herein with "screen" or "screening".

The term "expression level" as used herein refers to detecting the amount or level of expression of a biomarker of the present invention. The act of actually detecting the expression level of a biomarker refers to the act of actively determining whether a biomarker is expressed in a sample or not. This act can include determining whether the biomarker expression is up-regulated, down-regulated or substantially unchanged as compared to a control level expressed in a sample. The expression level in some cases may refer to detecting transcription of the gene encoding a biomarker protein and/or to detecting translation of the biomarker protein.

Expression of genes/transcripts and/or polypeptides encoded by the genes represented by the biomarkers of the present invention can be measured by any of a variety of methods known in the art. In general, expression of a nucleic acid molecule (e.g. RNA or DNA) can be detected by any suitable method or technique of measuring or detecting gene or polynucleotide sequence or expression. Such methods include, but are not limited to, polymerase chain reaction (PCR), reverse transcriptase PCR (RT-PCR), in situ PCR, quantitative PCR (q-PCR), in situ hybridization, Southern blot, Northern blot, sequence analysis, microarray analysis, detection of a reporter gene, or any other DNA/RNA hybridization platforms.

The term "quantifying" or "quantitating" when used in the context of quantifying transcription levels of a gene can refer to absolute or relative quantification. Absolute quantification can be achieved by including known concentration(s) of one or more target nucleic acids and referencing the hybridization intensity of unknowns with the known target nucleic acids (e.g. through the generation of a standard curve). Alternatively, relative quantification can be achieved by comparison of hybridization signals between two or more genes, or between two or more treatments to quantify the changes in hybridization intensity and, by implication transcription level.

Methods to measure protein/polypeptide expression levels of selected biomarkers in the present invention include, but are not limited to: Western blot, immunoblot, enzymelinked immunosorbant assay (ELISA), radioimmunoassay (RIA), immunoprecipitation, surface plasmon resonance, chemiluminescence, fluorescent polarization, phosphorescence, immunohistochemical analysis, liquid chromatography mass spectrometry (LC-MS), matrix-assisted laser desorption/ionization time-of-flight (MALDI-TOF), mass spectrometry, microcytometry, microarray, microscopy, fluorescence activated cell sorting (FACS), flow cytometry, and assays based on a property of the protein including but not limited to DNA binding, ligand binding, or interaction with other protein partners.

The term "biomarker" is used herein to refer to a molecule whose level of nucleic acid or protein product has a quantitatively differential concentration or level with respect to an aspect of a biological state of a subject. "Biomarker" is used interchangeably with "marker" herein. The level of the biomarker can be measured at both the nucleic acid level as well as the polypeptide level. At the nucleic acid level, a nucleic acid gene or a transcript which is transcribed from any part of the subject's chromosomal and extrachromosomal genome, including for example the mitochondrial genome, may be measured. An RNA transcript, or an RNA transcript including a primary transcript, a spliced transcript, an alternatively spliced transcript, or an mRNA of the biomarker may be measured. At the polypeptide level, a pre-propeptide, a propeptide, a mature peptide or a secreted peptide of the biomarker may be measured. A biomarker can be used either solely or in conjunction with one or more other identified biomarkers so as to allow correlation to the biological state of interest as defined herein. Specific examples of biomarkers covered by the present invention include proteins expressed on the cell surface in colon adenomas and adenocarcinomas but not in unaffected adjacent tissue. More specifically, biomarkers of the present invention include CLDN1, GPR56, GRM8, LY6G6D, TLR4 and SLCO1B3.

The term "cell" or "cells" is used synonymously herein and refers to in vitro cultures of mammalian cells grown and maintained as known in the art, as well as biological samples obtained from tumor specimens or normal specimens in vivo.

The term "sample" as used herein refers to any physical sample that includes a cell or a cell extract from a cell, a tissue, or an organ including a biopsy sample. The sample can be from a biological source such as a subject or animal, or a portion thereof, or can be from a cell culture. Samples from a biological source can be from a normal or an abnormal organism, such as an organism known to be suffering from a condition or a disease state such as a neoplasm, or any portion thereof. Samples can also be from any fluid, tissue or organ including normal and abnormal (diseased or neoplastic) fluid, tissue or organ. Samples from a subject or animal can be used in the present invention as obtained by the subject or animal and processed or cultured such that cells from the sample can be sustained in vitro as a primary or continuous cell culture or cell line. A "tumor sample" is a sample that includes at least one cell derived from at least one tumor.

The term "baseline level" or "control level" of biomarker expression or activity refers to the level against which biomarker expression in the test sample can be compared. In some embodiments, the baseline level can be a normal level, meaning the level in a sample from a normal patient. This allows a determination based on the baseline level of biomarker expression or biological activity, whether a sample to be evaluated for disease cell growth has a measureable increase, decrease, or substantially no change in biomarker expression as compared to the baseline level. The term "negative control" used in reference to a baseline level of biomarker expression generally refers to a baseline level established in a sample from the subject or from a population of individuals which is believed to be normal (e.g. non-tumorous, not undergoing neoplastic transformation, not exhibiting inappropriate cell growth). In other embodiments, the baseline level can be indicative of a positive diagnosis of disease (e.g. positive control). The term "positive control" as used herein refers to a level of biomarker expression or biological activity established in a sample from a subject, from another individual, or from a population of individuals, where the sample was believed, based on data from that sample, to have the disease (e.g. tumorous, cancerous, exhibiting inappropriate cell growth). In other embodiments, the baseline level can be established from a previous sample from the subject being tested, so that the disease progression or regression of the subject can be monitored over time and/or the efficacy of treatment can be evaluated.

The term "neoplasia", "cancer", "tumor", "cancerous", and "malignant" as used herein, refer to the physiological condition in mammals that is typically characterized by unregulated cell growth or the presence of tumors. Examples of cancer benefited by the present invention include, but are not limited to, tumors in tissue of the gastrointestinal (GI) tract such as adenomas and adenocarcinomas.

The term "about" as used herein is not intended to limit the scope of the invention but instead encompass the specified material, parameter or step as well as those that do not materially affect the basic and novel characteristics of the invention. The term "about" or "approximately" as used herein refers to being within an acceptable error range for the particular value as determined by one of ordinary skill in the art, which will depend in part on how the value is measured or determined, i.e. the limitations of the measurement system, i.e. the degree of precision required for a particular purpose, such as a pharmaceutical formulation. For example, "about" can mean within 1 or more than 1 standard deviation, per the practice in the art. Alternatively, "about" can mean a range of up to 20%, preferably up to 10%, more preferably up to 5% and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated, the term "about" meaning within an acceptable error range for the particular value should be assumed.

The term "gene expression product" or "expression product" as used herein refers to an RNA transcribed from a gene (either pre- or post-processing) or an amino acid (e.g. a polypeptide, protein, or peptide regardless of any secondary modifications, such as glycosylation, lipidation or phosphorylation) encoded by the gene and generated by the gene when the gene is transcribed (either pre- or post-modification) and translated. An agent is said to increase gene expression if the application of a therapeutically effective amount of the agent to a cell or subject results in an increase in either an RNA or polypeptide expression product or both. An agent is said to decrease gene expression if the application of a therapeutically effective amount of the agent to a cell or subject results in a decrease in either an RNA or polypeptide expression product or both.

The term "polynucleotide" as used herein refers to a polymeric molecule that has a backbone that supports bases capable of hydrogen bonding to typical polynucleotides. The polymer backbone presents the bases in a manner that is effective to allow such hydrogen bonding in a sequence specific fashion between the polymeric molecule and a typical polynucleotide, such as single-stranded DNA. Polymeric molecules include both single and double stranded DNA or RNA and can include polymers having backbone modifications. It includes the recited sequences as well as their complementary sequences, which can be easily ascertained by those of ordinary skill in the art.

The term "nucleic acid" as used herein may be double-stranded, single-stranded, or contain portions of both double and single stranded sequence. If the nucleic acid is single-stranded, the sequence of the other strand is also identifiable and thus the definition includes the complement of the sequence disclosed.

The term "polypeptide" as used herein refers to a compound made up of a single-chain of amino acid residues that are linked by peptide bonds. The term "protein" may be synonymous with the term "polypeptide" or may refer, in addition, to a complex of two or more polypeptides. Generally, polypeptides and proteins are formed predominantly of naturally occurring amino acids.

An "isolated polynucleotide" as used herein refers to a polynucleotide which is separated from other nucleic acid molecules which are present in the natural source of the polynucleotide. Preferably, an "isolated polynucleotide" is free of sequences which naturally flank the polynucleotide in the genomic DNA of the organism from which the nucleic acid is derived. An "isolated polynucleotide" is substantially free of other cellular material, gel materials, and culture medium when produced by recombinant techniques, or substantially free of chemical precursors or other chemicals when chemically synthesized. The polynucleotides of the present invention may be isolated from a variety of sources, such as PCR amplification from genomic DNA, mRNA, or cDNA libraries derived from the mRNA using standard techniques.

A "probe set" as used herein refers to a group of one or more polynucleotides that each selectively hybridize to the same target (for example, a specific genomic region or mRNA) that correlates with cancer diagnosis. As such, a single "probe set" may comprise any number of different isolated polynucleotides that selectively hybridize to a given target. A "probe" is a singular polynucleotide that selectively hybridizes to a target.

The term "agent" as used herein describes a composition, compound, chemical or extract that can be administered by the present invention. The chemical can be of any composition such as inorganic, organic, or a biomolecule. A biomolecule can be a molecule of any biological origin that can be found in or produced by, at least in part, a cell. This definition includes, but is not limited to, polypeptides, lipids, nucleic acids, carbohydrates and combinations thereof "Agent" is used interchangeably herein with "compound", "composition", "chemical", "drug", and "extract". In the present invention an agent or composition is formed from the addition of a contrast agent bound to at least one biomarker-specific ligand to a pharmaceutically acceptable carrier.

The phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19$^{th}$ ed.) describes formulations which can be used in connection with the subject invention.

For ease of administration, the subject compounds may be formulated into various pharmaceutical forms. As appropriate compositions there may be cited all compositions usually employed for systemically administering drugs. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules often represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution.

Recent studies have shown for other cancer types that targeted molecular imaging (fluorescence, MRI, CT, PET/SPECT) has great potential and, hence, can be applied to the screening of CRC. (Grassetto G, Capirci C, Marzola M C, Rampin L, Chondrogiannis S, Musto A, et al. Colorectal cancer: prognostic role of (18)F-FDG-PET/CT. Abdominal imaging 2011; Wang T D. Targeted imaging of flat and depressed colonic neoplasms. Gastrointestinal endoscopy clinics of North America 2010; 20:579-83; He X, Wang K, Cheng Z. In vivo near-infrared fluorescence imaging of cancer with nanoparticle-based probes. Wiley interdisciplinary reviews Nanomedicine and nanobiotechnology 2010; 2:349-66; ang X Y, Zhu Y Q, Wei B, Wang H. Expression and functional research of TLR4 in human colon carcinoma. The American journal of the medical sciences 2010; 339: 319-26; Abdelzaher E, Rizk A M, Bessa S S, Omer K M. Predictive value of immunohistochemical expression of claudin-1 in colonic carcinoma. Journal of the Egyptian National Cancer Institute 2011; 23:123-31; van Dam G M, Themelis G, Crane L M, Harlaar N J, Pleijhuis R G, Kelder W, et al. Intraoperative tumor-specific fluorescence imaging in ovarian cancer by folate receptor-alpha targeting: first in-human results. Nature medicine 2011; 17:1315-9; Rao J, Dragulescu-Andrasi A, Yao H. Fluorescence imaging in vivo: recent advances. Current opinion in biotechnology 2007; 18:17-25).

The inventors discovered cell-surface markers that distinguish CRC from surrounding unaffected GI tissues. Subsets containing as few as three of the markers were shown to cover nearly 100% of CRC samples with expression of at least one in each sample. Such markers can be used to improve current methods of CRC screening through the development of a novel, non-invasive molecular imaging method of detecting colon adenomas and adenocarcinomas with rapid acquisitions, high sensitivity and specificity, and without the need for general anesthesia. This molecular virtual colonoscopy, or "molecular colonography" can be used to identify patients that are in need of standard colonoscopy for biopsy or removal of CRC lesion and would be anticipated to have greater compliance.

The inventors identified six cell-surface markers (CLDN1, GPR56, GRM8, LY6G6D, TLR4 and SLCO1B3) with differentially high mRNA expression in patient samples of CRC compared to unaffected colon, and confirmed by IHC the high- and broad-expression of the six proteins among patient samples of colon adenoma and adenocarcinoma. Four of these marker proteins, claudin 1, metabotropic glutamine receptor 8, protein(s) Ly6-D/F and toll-like receptor 4 had higher expression in CRC compared to pathology scoring of epithelial cells in unaffected colon tissue.

Some staining in normal, unaffected epithelial cells was observed for all six markers. In the case of claudin 1, staining in normal colon samples has also been reported by Eman et al. (Abdelzaher E, Rizk A M, Bessa S S, Omer K M. Predictive value of immunohistochemical expression of claudin-1 in colonic carcinoma. Journal of the Egyptian National Cancer Institute 2011; 23:123-31). The epithelial layer of normal colon tissue is entirely covered by a thick mucosal layer which protects against pathogenic bacteria and helps in the movement of digested food by peristalsis. (Matsuo K, Ota H, Akamatsu T, Sugiyama A, Katsuyama T. Histochemistry of the surface mucous gel layer of the human colon. Gut 1997; 40:782-9). This mucus layer has been observed to be absent in areas of inflammation, and cancerous lesions, including adenomas and adenocarcinomas. (Matsuo K, Ota H, Akamatsu T, Sugiyama A, Katsuyama T. Histochemistry of the surface mucous gel layer of the human colon. Gut 1997; 40:782-9; Johansson M E, Larsson J M, Hansson G C. The two mucus layers of colon are organized by the MUC2 mucin, whereas the outer layer is a legislator of host-microbial interactions. Proceedings of the National Academy of Sciences of the United States of America 2011; 108 Suppl 1:4659-65).

Figure 4:
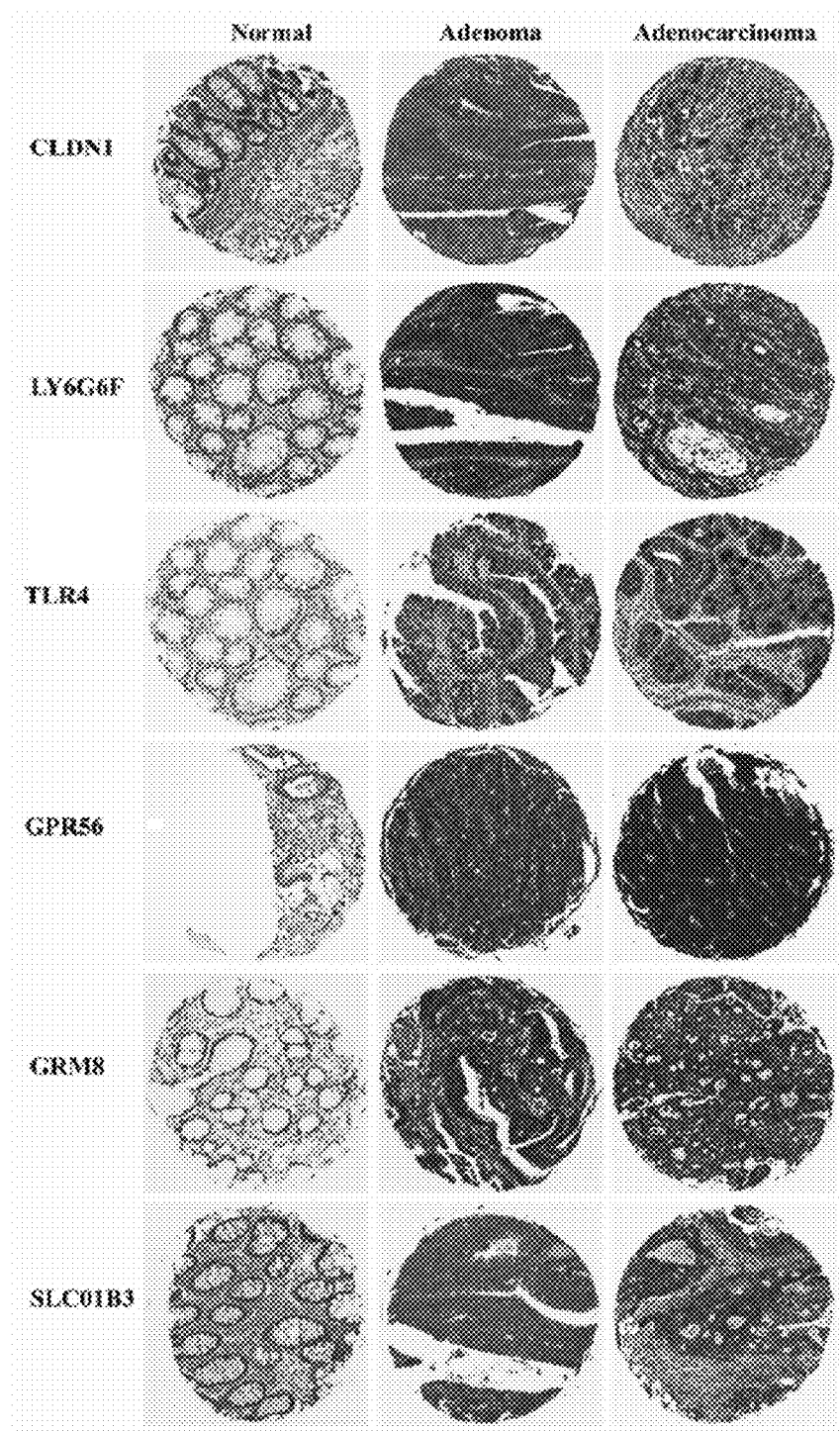
FIG. 4 is a series of representative images of marker immunohistochemical staining in patient samples of unaffected colon, adenoma and adenocarcinoma for CLDN1, LY6G6D, TLR4, GPR56, GRM8 and SLCO1B3.

In terms of the utility as molecular imaging target markers, it is not problematic that in some cases scoring of epithelial staining alone did not distinguish unaffected tissue from CRC. It is notable that in unaffected tissues the epithelial cell component has diffuse staining with a greater stromal component (FIG. 4). Also, unaffected colon epithelial cells are constantly secreting mucus and non-mucosal marker expression is restricted from a large percentage of the cell surface. Hence, the density of signal from bound imaging probes would be more diffuse in normal tissues compared to the more densely epithelial adenomas and adenocarcinomas.

Two markers, G-protein coupled receptor 56 and solute carrier organic ion transporter 1B3 were not distinguishable by pathology scoring unless the cytoplasmic surface occupied by mucin is considered, as these mucus secreting regions do not contain other cell-surface receptors. When the percentage of the surface of epithelial cells that express the marker protein was considered in the pathology scoring, none of the six markers had pathology scores≥4 in the unaffected colon tissue samples on the tissue microarray.

Claudin 1, the G-protein coupled receptor 56 and protein(s) Ly6-D/F had the broadest expression among adenoma samples with 79, 81 and 88% with pathology scores≥4. As few as three markers are needed to cover nearly all of the CRC samples with at least one of the three markers Claudin-1, toll-like receptor 4 and protein(s) Ly6-D/F expressed in 100% of the DNA microarray patient samples and 97% of the TMA samples with an IHC score of ≥4.

For each of the six markers, high mRNA was observed in a set of cell lines and DNA microarray data were largely in agreement with qRT-PCR results. By Western blot, a set of cells were identified with high protein expression of each marker, however, except for claudin-1, the mRNA data were not generally in agreement with the protein expression data in the same cell lines. This result indicates that for most of these markers, post translational regulation dominates gene expression. By immunocytochemistry, cell-surface expression was observed for each marker except for protein(s) Ly6-D/F. However, this does not indicate that surface expression will not be observed in CRC, since microenvironmental factors can also affect gene expression and subcellular localization.

The unaffected colonic epithelial layer is naturally covered by a mucus throughout the colon and rectum. In case of colon adenoma, adenocarcinoma, serrated adenoma, and neoplastic lesions mucus layer is greatly decreased. (Matsuo K, Ota H, Akamatsu T, Sugiyama A, Katsuyama T. Histochemistry of the surface mucous gel layer of the human colon. Gut 1997; 40:782-9; Johansson M E, Larsson J M, Hansson G C. The two mucus layers of colon are organized by the MUC2 mucin, whereas the outer layer is a legislator of host-microbial interactions. Proceedings of the National Academy of Sciences of the United States of America 2011; 108 Suppl 1:4659-65).

The mucus serves as protection against invading pathogenic bacterial flora and lubricates the colonic epithelial layer (mucosa). The mucus improves the access of molecular colonography probes to the lesions if delivered orally. Oral delivery of the molecular imaging probes also decreases the background signal and off-target effects which lead to increased sensitivity. In use, the ligand may be attached to the imaging ($^{18}$F-FDG-PET/CT, MRI, fluorescence imaging, functional time domain imaging) or therapeutic agent (photodynamic therapy) and used for diagnostic/prognostic or treatment purposes. (Wang S, Fan W, Kim G, Hah H J, Lee Y E, Kopelman R, et al. Novel methods to incorporate photosensitizers into nanocarriers for cancer treatment by photodynamic therapy. Lasers in surgery and medicine 2011; 43:686-95; Gupta A, Wang S, Pera P, Rao K V, Patel N, Ohulchanskyy T Y, et al. Multifunctional nanoplatforms for fluorescence imaging and photodynamic therapy developed by post-loading photosensitizer and fluorophore to polyacrylamide nanoparticles. Nanomedicine: nanotechnology, biology, and medicine 2011; Grassetto G, Capirci C, Marzola M C, Rampin L, Chondrogiannis S, Musto A, et al. Colorectal cancer: prognostic role of (18)F-FDG-PET/CT. Abdominal imaging 2011; Bipat S, Niekel M C, Comans E F, Nio C Y, Bemelman W A, Verhoef C, et al. Imaging modalities for the staging of patients with colorectal cancer. The Netherlands journal of medicine 2012; 70:26-34; Iftimia N, Iyer A K, Hammer D X, Lue N, Mujat M, Pitman M, et al. Fluorescence-guided optical coherence tomography imaging for colon cancer screening: a preliminary mouse study. Biomedical optics express 2012; 3:178-91; Wang T D. Targeted imaging of flat and depressed colonic neoplasms. Gastrointestinal endoscopy clinics of North America 2010; 20:579-83; McGinty J, Galletly N P, Dunsby C, Munro I, Elson D S, Requejo-Isidro J, et al. Wide-field fluorescence lifetime imaging of cancer. Biomedical optics express 2010; 1:627-40; Elson D, Requejo-Isidro J, Munro I, Reavell F, Siegel J, Suhling K, et al. Time-domain fluorescence lifetime imaging applied to biological tissue. Photochemical & photobiological sciences: Official journal of the European Photochemistry Association and the European Society for Photobiology 2004; 3:795-

801; He X, Wang K, Cheng Z. In vivo near-infrared fluorescence imaging of cancer with nanoparticle-based probes. Wiley interdisciplinary reviews Nanomedicine and nanobiotechnology 2010; 2:349-66).

EXAMPLE 1

Identification of Gene Markers

Through gene expression profiling of DNA microarray data from patient tissue samples of colon adenomas, adenocarcinomas, inflammatory bowel disease and unaffected tissues throughout the GI tract, the inventors have identified six putative cell surface proteins (CLDN1, GPR56. GRM8, LY6G6D, TLR4 and SLCO1B3) that are highly expressed in colon adenomas and adenocarcinomas but not in unaffected tissues. Two combinations of three markers (CLDN1, LY6G6D and TLR4, or CLDN1, GPR56 and TLR4) had 100% coverage of the 689 CRC samples in the microarrays, where at least one of the three markers is overexpressed in every sample.

Immunohistochemistry (IHC) was performed to confirm protein expression of these markers in patient samples of CRC and unaffected colon tissue. All of these markers demonstrated high expression in adenomas and adenocarcinomas. High expression was also observed in a fraction of the normal tissues, but the staining was more diffuse due to isolation to the epithelial component of the crypts and absence on the unaffected cell surface at the sites of mucosal secretions. Hence, these markers are valid targets for CRC specific molecular imaging agents. The three markers which demonstrated high expression are discussed below.

Claudin-1 (CLDN-1)

CLDN-1 is part of the 24 member claudin gene family and has a function in cell-cell adhesion interactions and maintenance of cell-membrane integrity. Claudins are integral transmembrane proteins involved in the formation of tight junctions in vertebrate animals. Epithelial tight junctions maintain the cellular electro-osmotic gradient and polarity with a role in the diffusion of ions, lipids, proteins, metabolites, etc. and function as a semi-permeable paracellular endothelial/epithelial diffusion barrier. (Steed E, Balda M S, Matter K. Dynamics and functions of tight junctions. Trends in cell biology 2010; 20:142-9; Anderson J M, Van Itallie C M. Physiology and function of the tight junction. Cold Spring Harbor perspectives in biology 2009; 1:a002584; Singh A B, Sharma A, Dhawan P. Claudin family of proteins and cancer: an overview. Journal of oncology 2010; 2010: 541957; Lal-Nag M, Morin P J. The claudins. Genome biology 2009; 10:235; Martin T A, Jiang W G. Loss of tight junction barrier function and its role in cancer metastasis. Biochimica et biophysica acta 2009; 1788:872-91).

Claudin 1 protein expression and involvement in tight junction formation are significantly altered during the process of carcinogenesis. (Singh A B, Sharma A, Dhawan P. Claudin family of proteins and cancer: an overview. Journal of oncology 2010; 2010:541957; Lal-Nag M, Morin P J. The claudins. Genome biology 2009; 10:235; Oliveira S S, Morgado-Diaz J A. Claudins: multifunctional players in epithelial tight junctions and their role in cancer. Cellular and molecular life sciences: CMLS 2007; 64:17-28; Gonzalez-Mariscal L, Latorre I J, Frese K K, Javier R T. Tight Junction Proteins and Cancer Tight Junctions. Springer US, 2006:116-34; Harhaj N S, Antonetti D A. Regulation of tight junctions and loss of barrier function in pathophysiology. The international journal of biochemistry & cell biology 2004; 36:1206-37; Wang X, Tully O, Ngo B, Zitin M, Mullin J M. Epithelial tight junctional changes in colorectal cancer tissues. The Scientific World Journal 2011; 11:826-41; de Oliveira S S, de Oliveira I M, De Souza W, Morgado-Diaz J A. Claudins upregulation in human colorectal cancer. FEBS letters 2005; 579:6179-85). Aberrant regulation of cell-cell adhesion, the diffusion barrier, and cellular organization and polarity are generally observed in cancer and inflammatory bowel disease. Elevated expression of claudin 1 has been observed in a majority of CRCs. (Martin T A, Jiang W G. Loss of tight junction barrier function and its role in cancer metastasis. Biochimica et biophysica acta 2009; 1788:872-91; Wang X, Tully O, Ngo B, Zitin M, Mullin J M. Epithelial tight junctional changes in colorectal cancer tissues. The Scientific World Journal 2011; 11:826-41; de Oliveira S S, de Oliveira I M, De Souza W, Morgado-Diaz J A. Claudins upregulation in human colorectal cancer. FEBS letters 2005; 579:6179-85; Grone J, Weber B, Staub E, Heinze M, Klaman I, Pilarsky C, et al. Differential expression of genes encoding tight junction proteins in colorectal cancer: frequent dysregulation of claudin-1, -8 and -12. International journal of colorectal disease 2007; 22:651-9; Miwa N, Furuse M, Tsukita S, Niikawa N, Nakamura Y, Furukawa Y. Involvement of claudin-1 in the beta-catenin/Tcf signaling pathway and its frequent upregulation in human colorectal cancers. Oncology research 2001; 12:469-76).

Lymphocyte Antigen 6, Locus Protein G6D (LY6G6D)

LY6G6D belongs to the leukocyte antigen-6 (LY6) superfamily and is located in the major histocompatibility complex (MHC) class III region of the genome. Lymphocyte antigen 6 complex locus protein G6d (Protein Ly6-D) is a 133 residue truncated version of the 297 amino acid Protein Ly6-F. Both are glycosylated cell-surface proteins. Protein Ly6-D is O-glycosylated and attached to the cell membrane with a glycosylphosphatidylinositol (GPI)-anchor. (Mallya M, Campbell R D, Aguado B. Transcriptional analysis of a novel cluster of LY-6 family members in the human and mouse major histocompatibility complex: five genes with many splice forms. Genomics 2002; 80:113-23; Shevach E M, Korty P E. Ly-6: a multigene family in search of a function. Immunology today 1989; 10:195-200; Williams A F. Emergence of the Ly-6 superfamily of GPI-anchored molecules. Cell biology international reports 1991; 15:769-77). Ly6-F is O-glycosylated and a single-pass type I membrane protein. Neither the DNA microarray probe used to identify this marker nor the monoclonal antibody used for IHC determination of protein expression distinguishes Proteins Ly6-D or -F from the other. Little is known about the biological function of these markers, however Ly6-D has been proposed to be involved in cell-cell interactions and intracellular signal transduction. (Calvanese V, Mallya M, Campbell R D, Aguado B. Regulation of expression of two LY-6 family genes by intron retention and transcription induced chimerism. BMC molecular biology 2008; 9:81). Not much is known about this target.

TLR4

TLR4 is part of the 10-member toll like receptor gene family in humans that functions in innate immune recognition. The toll-like receptor protein family is highly-conserved and their classification is based on their unique recognition of pathogen associated molecular patterns (PAMPs), e.g. lipopolysaccharides (LPS), lipoteichoic acids (LTA) and peptidoglycans (PGN). Unaffected human intestinal epithelial cells have low levels of TLR2 and TLR4 expression, whereas TLR3 and TLR5 are highly expressed in colon tissues. (Shang L, Fukata M, Thirunarayanan N, Martin A P, Arnaboldi P, Maussang D, et al. Toll-like receptor signaling in small intestinal epithelium promotes B-cell recruitment and IgA production in lamina propria. Gastroenterology 2008; 135:529-38). In inflammatory bowel diseases (IBD) such as ulcerative colitis, Crohn's disease and colitis associated cancer (CAC), TLR4 is observed to be prominently expressed and associated with a decremented mucus layer. (Einerhand A W, Renes I B, Makkink M K, van der Sluis M, Buller H A, Dekker J. Role of mucins in inflammatory bowel disease: important lessons from experimental models. European journal of gastroenterology & hepatology 2002; 14:757-65; Oostenbrug L E, Drenth J P, de Jong D J, Nolte I M, Oosterom E, van Dullemen H M, et al. Association between Toll-like receptor 4 and inflammatory bowel disease. Inflammatory bowel diseases 2005; 11:567-75; Cario E, Podolsky D K. Differential alteration in intestinal epithelial cell expression of toll-like receptor 3 (TLR3) and TLR4 in inflammatory bowel disease. Infection and immunity 2000; 68:7010-7; Sansonetti P J. War and peace at mucosal surfaces. Nature reviews Immunology 2004; 4:953-64; Fyderek K, Strus M, Kowalska-Duplaga K, Gosiewski T, Wedrychowicz A, Jedynak-Wasowicz U, et al. Mucosal bacterial microflora and mucus layer thickness in adolescents with inflammatory bowel disease. World journal of gastroenterology: WJG 2009; 15:5287-94). IBD patients are at high risk to develop adenocarcinoma. (Itzkowitz S H, Yio X. Inflammation and cancer IV. Colorectal cancer in inflammatory bowel disease: the role of inflammation. American journal of physiology Gastrointestinal and liver physiology 2004; 287:G7-17). In addition, TLR4 is up-regulated in CRC. (Itzkowitz S H, Yio X. Inflammation and cancer IV. Colorectal cancer in inflammatory bowel disease: the role of inflammation. American journal of physiology Gastrointestinal and liver physiology 2004; 287:G7-17).

The inventors have identified and validated potential cell surface markers for the targeting of diagnostic and therapeutic molecular probes. Protein expression in patient samples was confirmed for all six markers by IHC. As a secondary validation, expression of the 6 markers was determined in 8 colon cancer cell lines (COL 205, HCT15, HCT116, HT 29, KM12C, KM12SM, SW480 and SW620) by quantitative real-time RT-PCR (qRT-PCR), Western blot and immunocytochemistry (ICC). High- and low- or non-expressing cell lines were identified for each marker.

Materials and Methods

Cell Culture

HT29, HCT15 and SW620 human colon cancer cell lines were obtained from the DCTD Tumor Cell Line Repository (NCI at Fredrick, Md.), HCT116 and SW480 cells were obtained from the ATCC (American Type Culture Collection, Manassas, Va.) and KM12C and KM12SM cells were obtained from the MD Anderson Cancer Center (Dr. I. Fidler laboratory). All the eight cell lines were cultured in RPMI1640 media containing 300 mg/L L-Glutamine (Life Technologies, Invitrogen), 10% fetal bovine serum (Atlanta Biologicals), 10,000 units/ml penicillin, and 10,000 µg/ml streptomycin, and were incubated 5% $CO_2$ at 37° C. Throughout this study, the morphology and growth characteristics of these cells were monitored by microscopy.

DNA Microarray Expression Profiling

Compilation and quality control assessments of public and internal datasets were carried out in the Microarray Lab in the Moffitt Molecular Genomics Core Laboratory. DNA microarray data was assembled from 689 patient samples which include 432 adenocarcinomas, 39 adenomas, 16 inflammatory bowel disease, and samples from the following unaffected tissues: 178 colon, 6 small intestine, 4 stomach, 4 esophagus, 4 trachea, 3 oral mucosa and 3 tonsil. Data were filtered using a list of 3,800 genes that we had previously compiled from NCBI Gene Expression Omnibus database to be fortified for cell-surface genes. From this set, data for 1085 genes were extracted that had differentially high expression in tumor relative to unaffected tissue samples. Data for genes were sorted by degree of differential expression and the highest ranked genes were evaluated for potential use as cell-surface markers. The top six cell-surface genes were selected for further validation. TLR4 and/or GRM8 were shown to be expressed in 100% of the colon adenomas and adenocarcinomas in this dataset. To confirm protein expression, immunohistochemistry of normal (n=15) and CRC (16 adenoma and 60 adenocarcinoma) patient tissue samples and 26 colon cancer cell lines was performed. All six of the markers had high protein expression in adenomas and adenocarcinomas relative to generally low protein expression in normal colon. Further validation was performed by determining mRNA (qRT-PCR) and protein expression (Western blot and immunocytochemistry) of these markers in nine colon tumor cell lines (COLO-205, DIFI, HCT15, HCT116, HT-29, KM12C, Km12SM, SW480 and SW620).

Quantitative Real-Time Reverse-Transcriptase Polymerase Chain Reaction (qRT-PCR)

RNA extractions were performed on cell lines using the RNeasy®Mini Kit (Qiagen) following the manufacturer's instructions. RNA concentration and purity was determined by $A_{260}/A_{280}$ ratio using the Nanodrop Spectrophotometer, ND-1000. qRT-PCR was performed using the Smart Cycler (Cephid, Sunnyvale, Calif.) using a β-actin (ACTB) primer as an internal standard. Primer sets were designed for each marker (Table 1). The QuantiTect SYBR®Green RT-PCR Kit (Qiagen) was used for qRT-PCR. During each experiment reactions were performed using template without the RT step and with no-template added as controls. The following conditions for thermocycling were used: Stage 1 was held at 50° C. for 20 min for completion of the RT reaction; stage 2 was held at 95° C. for 15 min for initial denaturing of the cDNA; stage 3 cycled through three temperatures for PCR amplification, starting with 94° C. for 15 sec, 60° C. for 30 sec and 72° C. for 30 sec; and stage 4 included a melt curve for quality control, starting at 60° C. and ending at 95° C. Each experiment was repeated 3 times to determine reproducibility.

TABLE 1

Primer set for targets genes used in qRT-PCR from Integrated DNA Technologies (IDT), Inc. USA

| Target Gene | Accession No. | Primer Sequence (5' to 3') | Product Size (bp) |
| --- | --- | --- | --- |
| TLR4 | NT_008470.19 | forward tgg cca ttg ctg cca aca tca t (SEQ ID NO: 1) reverse tca aag ata cac cag cgg ctc t (SEQ ID NO: 2) | 113 |

TABLE 1 -continued

Primer set for targets genes used in qRT-PCR from Integrated DNA Technologies (IDT), Inc. USA

| Target Gene | Accession No. | Primer Sequence (5' to 3') | Product Size (bp) |
|---|---|---|---|
| GPR56 | | forward agt tct ggg cct ttg gca ttc a (SEQ ID NO: 3) reverse agc aca atg caa ggc aca cag t (SEQ ID NO: 4) | |
| GRM8 | AY608335 | forward tgt gtt tca gct atg cag ccc t (SEQ ID NO: 5) reverse act tgg gcg ctg tga cag att t (SEQ ID NO: 6) | 90 |
| CLDN1 | NM_021101.4 | forward tgg aaa ggg tgt tgg cat tgg (SEQ ID NO: 7) reverse gca gcc aaa tgc ctt gct caa (SEQ ID NO: 8) | 92 |
| SLCO1B3 | NM_019844 | forward ttg gct ttg cac tgg gat ctc t (SEQ ID NO: 9) reverse aac caa gcc acc aag ctc caa (SEQ ID NO: 10) | 121 |
| LY6G6D | NM_021246 | forward atc ttg ctc agc tcc ctg ct (SEQ ID NO: 11) reverse tca cgg cct ctt tgc aag aac t (SEQ ID NO: 12) | 97 |

Immunohistochemistry (IHC) of Tissue Microarray (TMA)

The colon cancer tissue microarray (TMA) was constructed at the Moffitt Tissue Core and contained cores from 46 unaffected colon samples, 26 adenomas, 91 adenocarcinomas and 26 colon tumor cell line samples. The formalin-fixed paraffin embedded tissue samples were first examined and graded after hematoxylin and eosin (H&E) staining as being unaffected colon, colon adenoma, or adenocarcinoma. Primary antibody optimizations were carried out by titrating antibodies at various dilutions on control tissues recommended by the manufacturer (Table 2). Slides were stained using a Ventana Discovery XT automated system (Ventana Medical Systems, Tucson) as per the manufacturer's protocol using proprietary reagents. Slides were deparaffinized on the automated system with EZ Prep solution (Ventana). The 4 min Protease 1 enzymatic retrieval method was used (Ventana). Primary antibodies were diluted using diluent (Carpenteria, CA) at the optimal ratio listed in (Table 2) and incubated for 60 min. The appropriate anti-mouse or anti-rabbit secondary antibody (Ventana) was used for a 16 min incubation. The Ventana OmniMap kit detection system was used first and then slides were counterstained with hematoxylin. Following staining, slides were dehydrated and coverslipped. Slide were scored by two pathologists (D.C. and A.S.L.) and each sample given a numerical score using the following equation: Score (0-9)=Intensity×Cellularity; where Intensity scores of 0=negative, 1=weak, 2=moderate and 3=strong staining; and Cellularity scores represent the percentage of epithelial cell staining, with 0=0%, 1=1-33%, 2=34-66% and 3=66-100% staining observed throughout the sample.

Western Blot

Protein was isolated from the colon cancer cell lines cultured in three 75 cm$^2$ flasks per line at 70% to 80% confluence (~2×10$^6$ cells per flask) by first washing with phosphate buffered saline (DPBS). Then, cell lysates were prepared by incubating for 10 min at RT in insect cell lysis buffer (10 mM Tris pH 7.5, 130 mM NaCl, 1% Triton X-100, 10 mM NaF, 10 M sodium phosphate, 10 mM sodium pyrophosphate) followed by addition of 4× protease inhibitor cocktail (Cat# P2714, Sigma) to 1× final concentration. Lysate was collected by gentle scraping and stored on ice. Lysates were sonicated using an intermediate frequency level for 5 seconds followed by centrifugation at 4° C. for 10 min at 13,000 rpm. Clear lysate supernatant was separated and protein concentration determined using the BCA protein assay (Thermo Scientific) and the Multiskan MCC/340 (Fisher Scientific) plate reader at 570 nm absorbance.

Western blotting was performed as follows: 25 µg protein was fractionated by size on SDS/PAGE gels (Invitrogen) and then transferred to nitrocellulose membranes (Bio-Rad Laboratories). The membrane was blocked by incubation in 2% BSA for an hour, followed by a 2 h incubation with primary antibody (Table 2), followed by incubation with appropriate secondary antibody conjugated to horseradish peroxidase. The antigen-antibody reaction resulted in chemiluminescence which was exposed on X-ray film.

TABLE 2

Antibodies and Dilutions for IHC, Western blot and ICC

| Marker | Product | Species | Dilution | Control Tissue | Size kDa |
|---|---|---|---|---|---|
| CLDN1 | C104910, LifeSpan BioSciences, Inc. | Mouse monoclonal | 1:600 | Colon (N) | 95 |
| TLR4 | Mab 14783, R&D Systems | Mouse monoclonal | 1:200 | Prostate Cancer | 75 |
| LY6G6D/F* | HPA008053, Sigma-Aldrich | Rabbit polyclonal | 1:20 | Normal testis | 102 |

TABLE 2-continued

Antibodies and Dilutions for IHC, Western blot and ICC

| Marker | Product | Species | Dilution | Control Tissue | Size kDa |
|---|---|---|---|---|---|
| GPR56 | TM7XN1/ GPR56, Thermo Scientific | Rabbit polyclonal | 1:100 | Brain GBM | 18 |
| GRM8 | Ab53094, Abcam | Rabbit polyclonal | 1:100 | Brain | 78 |
| SLCO1B3 | HPA004943, Sigma-Aldrich | Rabbit polyclonal | 1:1250 | HepatoCa | 37 |

*Note:
This antibody will hybridize to both Ly6-D and Ly6-F proteins.

Immunocytochemistry (ICC)

Colon cancer cells were seeded on glass coverslips in twelve well plates at a density of $2 \times 10^4$ cells per well. Cells attached overnight and were then fixed in fresh 4% paraformaldehyde (USB Corporation) for 20 minutes at room temperature, followed by 3 washes in DPBS (GIBCO). Fixed cells were rinsed three times for five minutes with 0.75% glycine in DPBS to quench the paraformaldehyde and blocked with 2% BSA in DPBS for one hour followed by three 15 minute washes. Primary antibodies (Table 2) were diluted 1:50 in 2% BSA and 5 µg/ml WGA, added to fixed cells and incubated for 2 hours followed by three 10 minute washes. Secondary antibody incubations were performed using 1:2000 dilutions by 2% BSA in DPBS for an hour, followed by three 10 minute washes. The second wash buffer included DAPI nuclear stain at 1:10,000 dilution. Coverslips were mounted on glass slides with Prolong@Gold-antifade mounting media (Invitrogen). Allowed to sit overnight in the dark at 4° C. and then imaged on the confocal microscope (Leica) located in the Moffitt Analytic Microscopy Core.

Results

Cell-Surface Marker Identification

By expression profiling of DNA microarray data, six putative cell surface markers (CLDN1, LY6G6D, GPR56, GRM8, SLCO1B3 and TLR4) were identified to be highly and broadly expressed as mRNA among patient colon adenoma and adenocarcinoma samples relative to other unaffected tissues in the gastrointestinal (GI) tract (unaffected colon, small intestine, stomach, esophagus, trachea, oral mucosa, tongue and tonsil). FIG. 2 shows boxplot expression profiles for the six markers and note the log scale on the Y-axis. In FIG. 2A, note that the median values for CLDN1 expression in adenocarcinoma (AC) and adenoma are higher than those of the unaffected (normal) colon, small intestine and stomach. However, unlike the other markers, expression in oral and throat tissues are also high. For all six markers AC median values had a broader range from very low to very high, indicating that possibly no single marker will be highly expressed in every patient and that perhaps a combination of markers could be used to cover the entire range of colon cancer. Likewise, note that the set of "normal" samples also has a broad range of expressing values for each marker, indicating that there could be some unknown pathology may be indicated in a subset of those samples. The inflammatory bowel disease (IBD) samples had elevated expression of four of the six markers (CLDN1, GPR56, SLCO1B3 and TLR4).

Figure 3:
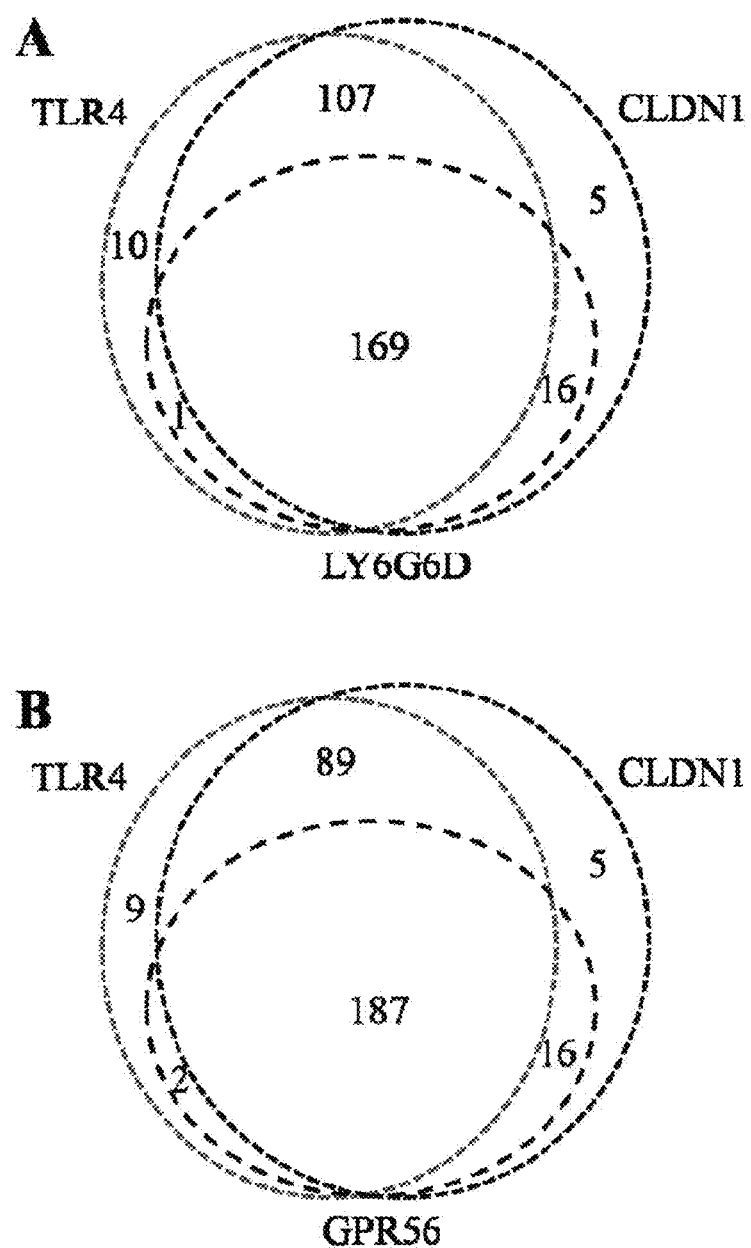
FIG. 3A-B is a series of Venn diagrams showing 100% coverage of 308 patient samples by sets of three markers using DNA microarray expression data: (A) CLDN1 LY6G6D and TLR4; (B) CLDN1, GPR56 and TLR4.

Based on expression relative to the "normal" unaffected colon values, CLDN1 had the highest (96%) overexpression in the colon adenoma and adenocarcinoma samples combined, (n=308) (Table 3). The top three markers in terms of overexpression were CLDN1, TLR4 and GPR56, and at least one of these three markers is overexpressed in 100% of the CRC samples surveyed. See the Venn diagram in FIG. 3A. When combining the fourth highest marker in terms of overexpression, LY6G6D, with the top two markers, the same observation is made (2B).

TABLE 3

Colon tumor coverage by marker DNA microarray expression

| Target expressed | % of tumor |
|---|---|
| CLDN1 | 96.4% |
| TLR4 | 93.2% |
| LY6G6D | 60.4% |
| GPR56 | 66.6% |
| GRM8 | 45.5% |
| SLCO1B3 | 6.8% |

Confirmation of Marker Protein Expression

To confirm protein expression of the six identified CRC cell-surface markers (vide supra), immunohistochemistry (IHC) was performed for each marker using a tissue microarray containing colon adenoma, adenocarcinoma and unaffected colon tissue samples from patients. FIG. 4 shows representative IHC staining of unaffected colon tissue samples, colon adenomas and colon adenocarcinomas for each cell-surface marker. Table 4 shows the pathologist (A.S.L. and D.C.) TMA scoring for protein expression of each marker.

TABLE 4

Immunohistological scoring of marker expression in patient tissue samples

| Marker | Tissue type | Patient Tissue Samples (n) | Pathology Score | | | | | | % ≥ 4 |
|---|---|---|---|---|---|---|---|---|---|
| | | | 0 | 1 | 2 | 3 | 4 | 6 | 9 | |
| CLDN1 | Normal | 25 | 1 | 1 | 8 | 15 | 0 | 0 | 0 | 0 |
| | Adenoma | 24 | 1 | 0 | 0 | 4 | 0 | 15 | 4 | 79.2 |
| | Adenocarcinoma | 80 | 0 | 0 | 6 | 20 | 8 | 28 | 18 | 67.5 |
| LY6G6F | Normal | 13 | 0 | 0 | 0 | 7 | 0 | 6 | 0 | 46.2 |
| | Adenoma | 16 | 0 | 0 | 0 | 2 | 2 | 6 | 6 | 87.5 |
| | Adenocarcinoma | 59 | 0 | 0 | 9 | 16 | 1 | 20 | 13 | 57.6 |
| TLR4 | Normal | 15 | 0 | 0 | 11 | 3 | 0 | 0 | 1 | 6.6 |
| | Adenoma | 16 | 0 | 0 | 2 | 4 | 0 | 8 | 2 | 62.5 |
| | Adenocarcinoma | 60 | 2 | 0 | 16 | 15 | 1 | 20 | 6 | 45 |
| GPR56 | Normal | 13 | 0 | 0 | 1 | 1 | 0 | 11 | 0 | 84.6 |
| | Adenoma | 21 | 0 | 0 | 0 | 4 | 0 | 8 | 9 | 80.9 |
| | Adenocarcinoma | 68 | 0 | 0 | 0 | 13 | 0 | 18 | 37 | 80.9 |

TABLE 4-continued

Immunohistological scoring of marker expression in patient tissue samples

| Marker | Tissue type | Patient Tissue Samples (n) | Pathology Score | | | | | | % ≥ 4 |
|---|---|---|---|---|---|---|---|---|---|
| | | | 0 | 1 | 2 | 3 | 4 | 6 | 9 | |
| GRM8 | Normal | 23 | 0 | 0 | 0 | 17 | 0 | 6 | 0 | 26.1 |
| | Adenoma | 22 | 0 | 0 | 3 | 5 | 0 | 8 | 6 | 63.3 |
| | Adenocarcinoma | 75 | 0 | 0 | 10 | 26 | 4 | 29 | 6 | 52 |
| SLCO1B3 | Normal | 16 | 3 | 9 | 2 | 1 | 0 | 1 | 0 | 6.2 |
| | Adenoma | 22 | 2 | 1 | 8 | 9 | 0 | 2 | 0 | 9.1 |
| | Adenocarcinoma | 75 | 8 | 12 | 34 | 16 | 0 | 5 | 0 | 6.7 |

As described in Materials and Methods, the pathology scores are a multiple of staining intensity and the degree of epithelial cell positivity (i.e. heterogeneity of staining). Hence, scores ≤3 represent samples with either low staining levels, or low staining coverage within the sample; and scores ≥4 represent samples with at the very least moderate staining levels and coverage. Based on the pathology scores, claudin 1 and toll-like receptor 4 were the only two markers where adenomas and adenocarcinomas were greatly distinguished from unaffected normal samples. For claudin 1, 79% and 68% of adenoma and adenocarcinoma samples scored ≥4 respectively, and 0% of unaffected "normal" samples scored ≥4. Similarly for toll-like receptor 4, 63% and 45% of adenomas and adenocarcinomas scored ≥4, with only 7% of unaffected samples scoring ≥4. Although the metabotropic glutamine receptor 8 and protein(s) Ly6-D/F were less able to distinguish CRC from unaffected tissues, these markers scored 26% and 46% ≥4 respectively for unaffected colon tissue, compared to 63% and 88% ≥4 for adenomas. G-protein coupled receptor 56 and solute carrier organic ion transporter 1B3 did not distinguish CRC from unaffected colon tissue by pathology score alone.

The epithelial cell component of unaffected tissues is diffuse, with a high percentage of stromal cells in each sample, compared to CRC adenoma and adenocarcinomas with a high density of epithelial cells and, hence, a greater density of staining of all six markers (FIG. 4). Additionally, if the cytoplasmic surface occupied by mucin is considered by the pathologist, the homogeneity of marker expression on the cell-surface is decreased and the scores for all six markers decrease to a score of 0% ≥4.

At least one of the two protein markers claudin 1 or toll-like receptor 4 scored≥4 in 83% of adenoma and adenocarcinoma cores in the CRC TMA. At least one of the three markers claudin-1, toll-like receptor 4, and protein(s) Ly6-D/F were expressed in 97% of the tissue samples.

Marker Expression in Cell Lines

For further validation, colon tumor cell lines were characterized for expression of the six markers. DNA microarray datasets for eight different human colon carcinoma cell lines (COL0205, HCT15, HCT116, HT29, KM12C, KM12SM, SW480 and SW620) were analyzed for marker mRNA expression. GPR56 expression was observed in all 8 lines and expression of each marker was observed in at least one of the eight tumor lines (Table 5). For a more quantitative measure of mRNA levels, qRT-PCR was performed to determine expression of each marker in these 8 lines and ACTB normalized expression values are reported in FIG. 6. With a few minor exceptions, the qRT-PCR mRNA expression values were generally in agreement with the DNA microarray values. CLDN1 and GPR56 were both broadly expressed among cell lines, while GRM8, LY6G6D/F and TLR4 were expressed in a few individual lines. While SLCO1B3 had high qRT-PCR ACTB normalized expression values across the set of cell lines, only the two highest were highly expressed in the normalized DNA microarray dataset.

TABLE 5

Marker DNA microarray expression in colon tumor cell lines

| Cell Line | Gene | | | | | |
|---|---|---|---|---|---|---|
| | TLR4 | LY6G6D | GPR56 | GRM8 | SLCO1B3 | CLDN1 |
| COLO-205 | * | — | ** | highest | — | — |
| HCT15 | — | — | lowest | — | — | — |
| HCT116 | — | — | lowest | — | — | ** |
| HT-29 | ** | — | ** | — | — | * |
| KM12 | — | — | * | — | *** | *** |
| KM12S | — | — | ** | — | *** | *** |
| SW-480 | ** | *** | ** | — | — | *** |
| SW-620 | ** | ** | ** | — | — | *** |

Figure 5:
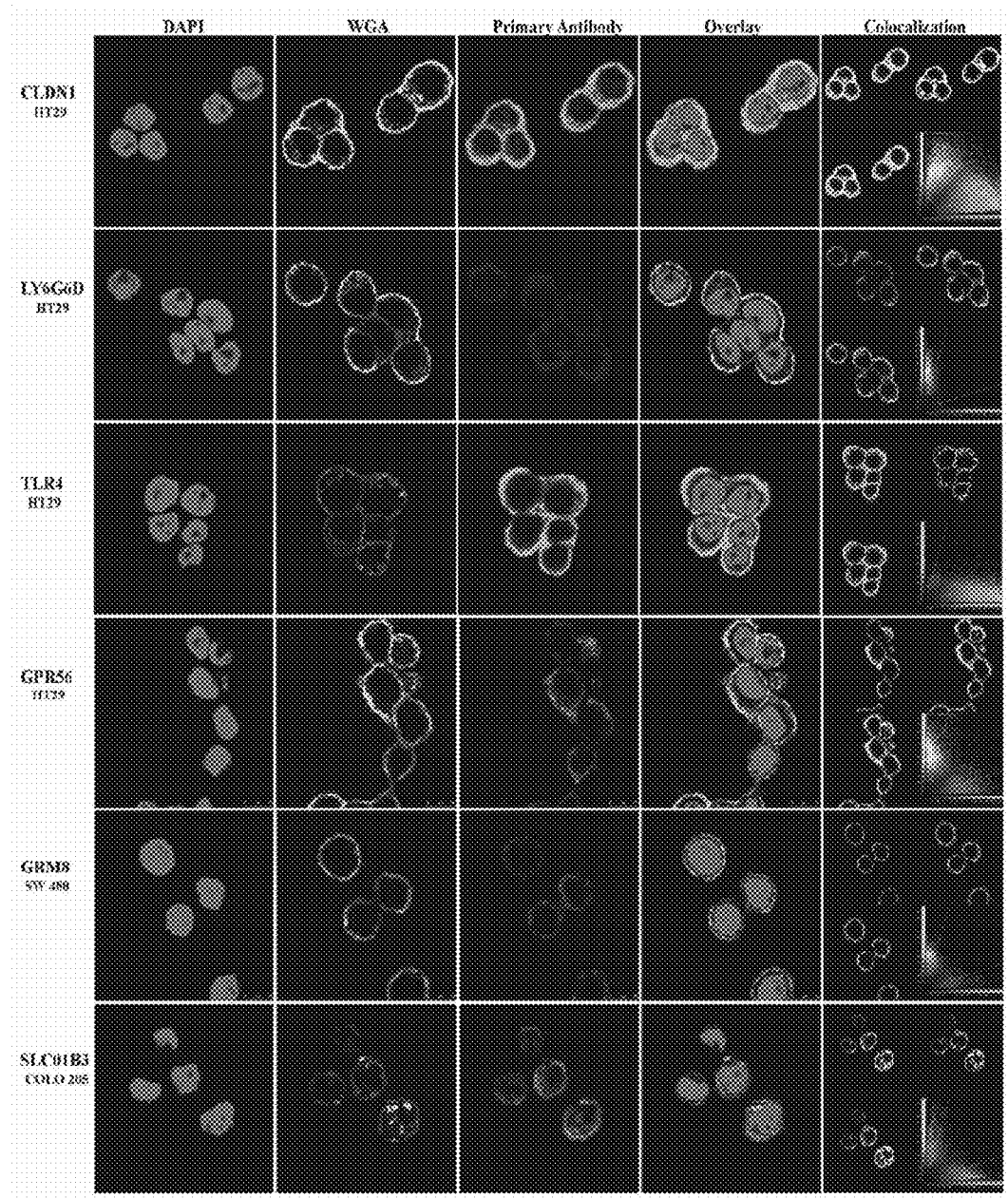
FIG. 5 is a series of images of immunohistochemistry showing cell surface expression of marker proteins in human CRC tumor cell lines. The markers examined included: CLDN1, LY6G6D, TLR4, GPR56, GRM8 and SLCO1B3.
Figure 7:
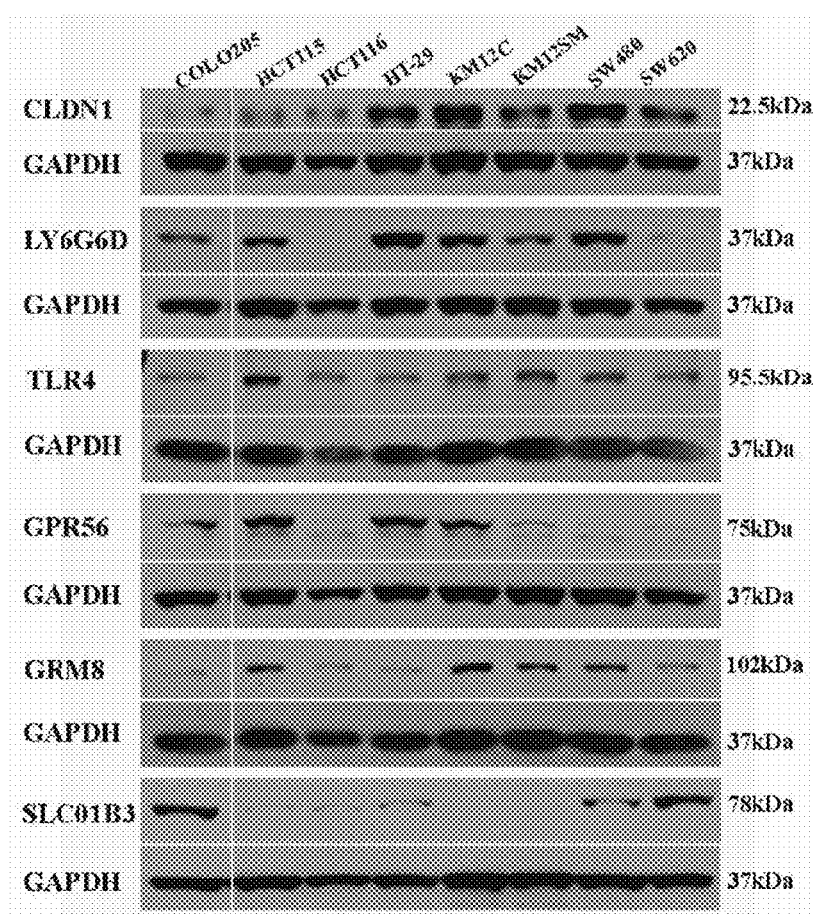
FIG. 7 is an image of a Western blot of marker expression in human colorectal cancer lines. The markers examined included: CLDN1, LY6G6D, TLR4, GPR56, GRM8, and SLCO1B3. The colorectal cancer lines used included: COLO-25, HCT15, HCT116, HT-29, KM12SM, SW480 and 620.

Western blots were performed to determine marker protein expression in the eight cell lines (FIG. 7). Despite the general agreement in levels among the two mRNA expression datasets, the protein expression levels observed in the Western blots were not in agreement with the mRNA levels except for one marker. Claudin 1 protein levels were comparable to CLDN1 mRNA levels, suggesting that regulation of Claudin 1 protein occurs at the level of transcription. As described above GPR56 mRNA was broadly detected among the cell lines, but corresponding protein levels were only detected at high levels in 4 of the eight cell lines. While GRM8, LY6G6D/F and TLR4 mRNA was sparsely detected among the cell lines but a broader protein expression pattern was observed by Western blot indicating that protein levels for these markers are likely regulated post-translationally in this set of colon cancer cells. Remarkably, no protein was detected in the two cell lines with high mRNA expression of SLCO1B3. To confirm protein expression on the cell-surface, immunocytochemistry (ICC) was performed using cells that had high protein levels for each marker. By ICC, cell surface expression of claudin 1, G-protein coupled receptor 56 and toll-like receptor 4 protein was observed in HT-29 cells; metabotropic glutamine receptor 8 in SW480 cells; and solute carrier organic anion transporter 1B3 in COLO-205 cells (FIG. 5). Surface expression of protein(s) Ly6-D/F was not observed on the surface of any of the cell lines surveyed.

To summarize, the inventors have identified and confirmed protein expression of six cell-surface markers that are differentially expressed in colon adenomas and adenocarcinomas relative to surrounding unaffected colon tissue. These markers can be used to develop molecular imaging probes for screening and detection of lesions by molecular virtual colonoscopy, or 'molecular colonography.' In addition, cell lines were identified that express mRNA and protein for each marker. Cell surface expression was observed for all but one marker.

EXAMPLE 2

Development of MRI and CT Contrast Agents

Patients may be screened for colon cancer with either CT- or MR-based molecular colonography (virtual colonoscopy, VC) using targeted oral contrast reagents that specifically bind to and identify pre-cancerous lesions with high conspicuity. This oral reagent is a cocktail mixture of individual agents, each identifying a phenotypic subset of pre-cancerous and cancerous lesions. The first marker used to develop MRI and CT contrast agents (CA) targeted against it is TLR4, which is highly expressed in ~50% of human CRC. In parallel, ligands for additional targets are developed. The agents are comprised of biocompatible and biostable CA that are decorated with multiple copies of the TLR4 specific synthetic ligand. The CA must be biocompatible and be capable of being imaged by either CT or MRI in the GI tract. Additionally, the CA and ligand must be stable in the digestive tract and achieve selectivity using multivalent (effectively irreversible) binding. CAs may carry contrast-generating cargo that can be optimized to maximize conspicuity.

The high sensitivity/low specificity/low-impact screen described herein may identify those high-risk patients who should be further screened via colonoscopy. Colonoscopy is considered to be 100% specific and 98% sensitive. However, of the 1.2 million patients that undergo colonoscopy annually, only approximately 100,000 are found to have colon cancer at any stage. Thus, there are 1.1 million "unnecessary" procedures annually. Assuming a specificity of 30% for the pre-screening test described herein, an area under the ROC curve (AUROC) would be 65%, which would reduce the number of unnecessary procedures by approximately 330,000 annually. If the cost of the pre-screen is 5% that of colonoscopy, a test with 30% specificity would reduce the cost of colorectal screening by 28%. Additionally, the proposed method lends itself to higher compliance, which increases the numbers of actual patients who benefit from invasive colonoscopy, which in turn, should improve detection of early, resectable disease.

The agents are selectively targeted to CRC lesions thus providing increased contrast with decreased background interference, effectively increasing both the sensitivity and specificity relative to the current methods. While local T staging can be performed with high accuracy (~80%) by CT or MRI, the anatomical relation of primary lesion to mesorectal fascia in rectal tumors is most efficiently shown by MRI. (Dighe S, Swift I, Brown G. CT staging of colon cancer. Clinical Radiology. 2008; 63(12):1372-9; Bipat S, Glas A S, Slors F J M, Zwinderman A H, Bossuyt P M M, Stoker J. Rectal cancer: Local staging and assessment of lymph node involvement with endoluminal US, CT, and MR imaging—A meta-analysis. Radiology. 2004; 232(3):773-83; Klessen C, Rogalla P, Taupitz M. Local staging of rectal cancer: the current role of MRI. European Radiology. 2007; 17(2):379-89). Larger CRC tumors are readily detected by MR-C or CT-C, thus, the method described herein has the capability for detection of benign adenomas as well as adenocarcinomas. The multimodal fluorescence capability may also be used for intraoperative detection of tumor margins during resection. Developing both CT and MRI approaches provides an MRI alternative to patients suffering from renal failure, and a CT alternative to those having pacemakers, metallic implants, or adverse reactions to claustrophobic conditions. Targeted contrast agents add sensitivity and specificity to CT-C and/or MR-C without the need for cathartic bowel prep.

An emerging theme in targeting biochemistry is the increasing use of multiple copies of binding moieties (multivalency) to provide enhanced avidity and cooperativity. (Cairo C W, Gestwicki J E, Kanai M, Kiessling L L. Control of multivalent interactions by binding epitope density. Journal of the American Chemical Society. 2002; 124(8):1615-9; Handl H L, Vagner J, Yamamura H I, Hruby V J, Gillies R J. Lanthanide-based time-resolved fluorescence of in cyto ligand-receptor interactions. Analytical Biochemistry. 2004; 330(2):242-50). Multivalent ligands and nanoconstructs have been previously developed. (Mammen M, Choi S K, Whitesides G M. Polyvalent interactions in biological systems: Implications for design and use of multivalent ligands and inhibitors. Angewandte Chemie-International Edition. 1998; 37(20):2755-94; Vagner J, Xu L, Handl H L, Josan J S, Morse D L, Mash E A, et al. Heterobivalent ligands crosslink multiple cell-surface receptors: the human melanocortin-4 and delta-opioid receptors. Angew Chem Int Ed Engl. 2008; 47(9):1685-8; Xu L, Vagner J, Josan J, Lynch R M, Morse D L, Baggett B, et al. Enhanced targeting with heterobivalent ligands. Mol Cancer Ther. 2009; 8(8):2356-65; Barkey N M, Tafreshi N K, Josan J S, De Silva C R, Sill K N, Hruby V J, et al. Development of Melanoma-Targeted Polymer Micelles by Conjugation of a Melanocortin 1 Receptor (MC1R) Specific Ligand. J Med Chem. 2011; 54(23):8078-84; Rao V, Alleti R, Xu L, Tafreshi N K, Morse D L, Gillies R J, et al. A sucrose-derived scaffold for multimerization of bioactive peptides. Bioorg Med Chem. 2011; 19(21):6474-82. PMCID: 3197697).

Multivalent binding provides firm adhesion of the contrast agent to the neoplastic target, thus providing high specificity and sufficient contrast, even if particles are non-specifically absorbed in the GI tract or immobilized in formed stools. Multivalent binding enhances affinity by sharply increasing the number of cascading energy barriers encountered along the unbinding trajectory without adversely affecting the kinetics of bond formation. (Williams P M. Analytical descriptions of dynamic force spectroscopy: behaviour of multiple connections. Analytica Chimica Acta. 2003; 479(1):107-15). The enhanced binding strength of multiple uncorrelated bonds was demonstrated for a mucin-1 (Muc-1) targeting using anti-Muc-1 antibodies. (Sulchek T A, Friddle R W, Langry K, Lau E Y, Albrecht H, Ratto T V, et al. Dynamic force spectroscopy of parallel individual Mucin1-antibody bonds. Proceedings of the National Academy of Sciences of the United States of America. 2005; 102(46):16638-43). As the number of bonds increased from 1 to 3, the detachment force increased over a wide range of loading rates and the bound lifetimes increased from 280 sec for one bond to 320 d for the triply bonded case. Enhanced avidities were modeled by a Markovian sequence considering parallel load distribution and rupture/rebinding kinetics. Thus, multiple weak interactions cooperatively combine to yield high strength and specificity. The contrast agents (CA) described herein are functionalized to accommodate a range of ligand loading levels.

For CT, varying particle sizes of biocompatible gold nanoparticles (Nanoprobes Inc., CT) that were previously targeted to integrins in vivo were evaluated. For MRI, different formulations of Gd (III) chelates attached to a sucrose scaffold that were previously developed were evaluated. Both contrast agents have built-in attachment sites for targeting groups. Characterization involves determination of limits of detection by concentration using molar Hounsfield units (CT) and $T_1$ molar relaxivities (MRI), as well as stability as a function of pH, temperature and catalytic digestion. The construct formulation (composition and size) is suitably modulated to ensure sufficient conspicuity and biostability in an in vivo setting. Agents are evaluated for delivery by the oral route.

MRI Contrast Agents

MRI contrast agents were developed by synthesizing a novel sucrose scaffold based on the structure of Olestra™ and conjugating varying numbers of Gd(III)-DOTA chelates to the scaffold. Biostability studies in rats were performed using a version of the scaffold conjugated to NBD fluorescent dye (FIG. 8A) have demonstrated that the agent passes through the GI tract without being absorbed. After 48 h post gavage into rats, ~40% of the agent was retrieved from the feces by extraction and chromatographic purification. The remaining 60% was also unabsorbed, but the fluorescence was quenched (and undetected) due to nitro group reduction by flora present in the gut.

Figure 9:
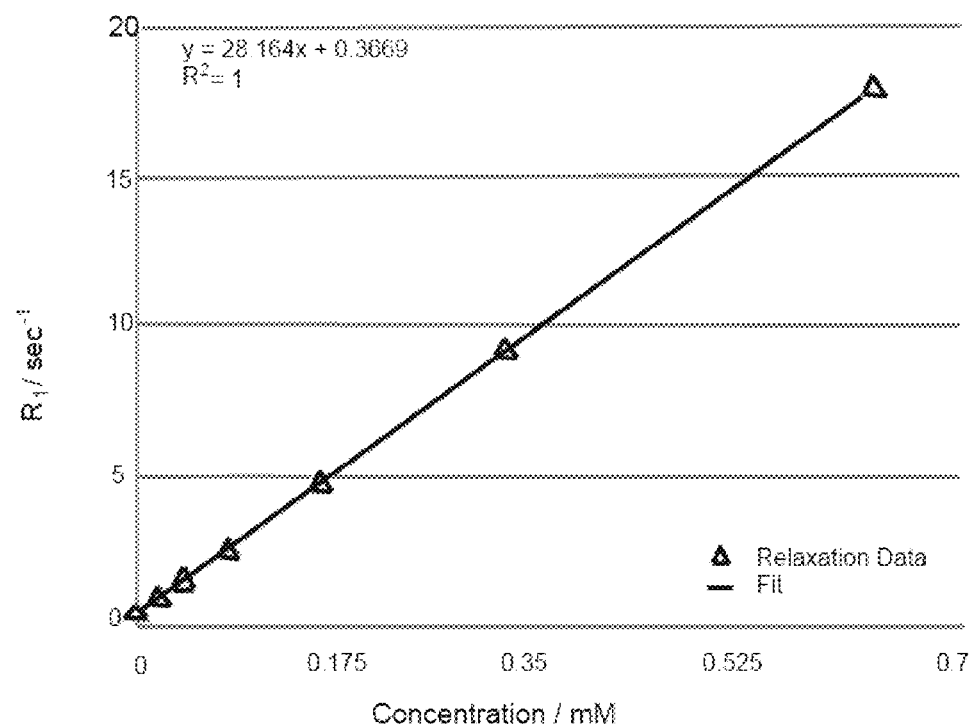
FIG. 9 is a graph depicting the linear regression of experimental phantom data (R1) as a function of concentration. The fitted value for molar relaxivity (r1) is 28.2 mM s−1. Relaxation experiments were accomplished with multiple TR spin echo experiments on two separate Eppendorf tube phantoms prepared with identical concentrations of Gd-DOTA-sucrose-8.

Initial MRI characterization of a Gd-sucrose construct bearing an average of 6.5 Gd-DOTA moieties was accomplished in phantom. An initial high concentration stock solution was prepared, and two separate phantoms were created by serial dilution. These phantoms were studied using progressive saturation experiments (PS). Nonlinear least squares regression allowed for the determination of the relaxation time constant ($T_1$) leading to the relaxation rate constant ($R_1 = 1/T_1$). FIG. 9 shows the relationship between the $R_1$ and [CA], where linear regression was used to determine an $r_1$.value of 28.2 mM sec$^{-1}$. This is approx. 6.5 times higher than GdDOTA itself, thus indicating that individual chelates are independently additive to the overall relaxivity of the construct.

Figure 8:
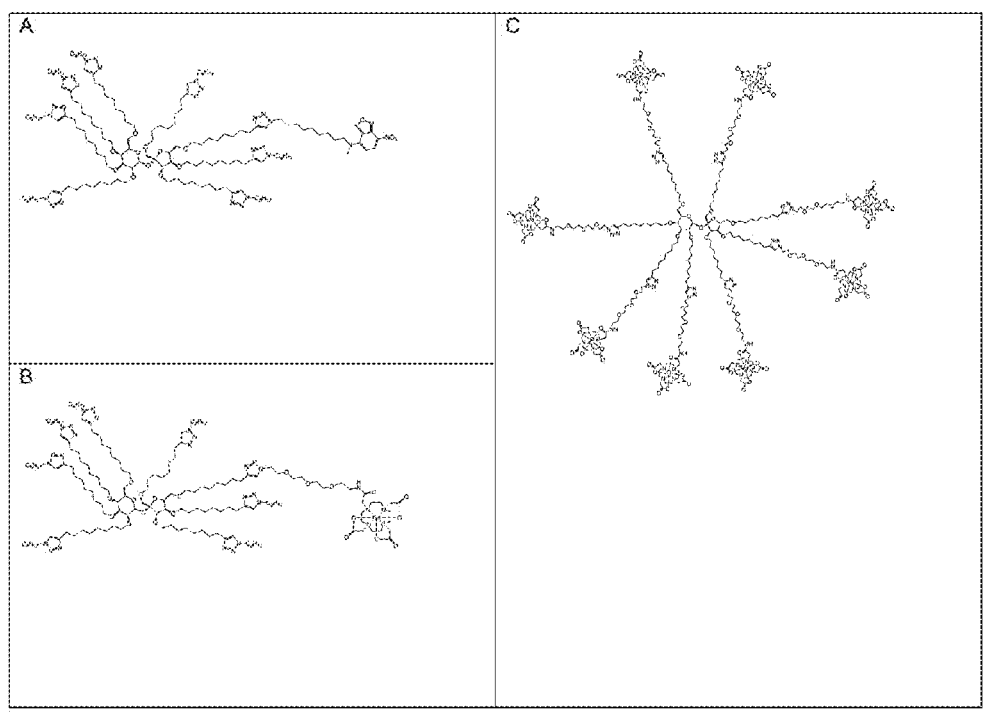
FIG. 8A-C is a series of images depicting the structures of sucrose scaffold compounds: (A) conjugated to a single NBD fluorescent dye; (B) conjugated to a single Gd(III)-DOTA chelate and (C) conjugated to 8 Gd(III)-DOTA chelates.

MRI studies were performed in C3H mice using a version of the scaffold containing a single Gd(III)-chelate (FIG. 8B) and a version containing an average of 6.5 chelates per scaffold (FIG. 8C). The agent was resuspended in 0.1 µM phosphate buffer, pH 7.4 and administered to animals by gavage. The high buffering may protect from de-methylation of the chelate by stomach acid. Animals were anesthetized and prepared for MR imaging by induction with isoflurane. The animals were placed in a mouse-specific holder within an Agilent 72 mm birdcage coil (Agilent Technologies Inc., Santa Clara, Calif.) and inserted into an Agilent ASR 310 7T MRI system for scanning, which typically required 1 hour.

Pre- and post-contrast imaging included scout (FLASH) scans with three-plane geometry, axial $T_2$-weighted Fast Spin Echo (FSEMS), with TR/TE=2800/48 ms, was acquired with multiple slices (typically 25) in order to determine an appropriate orientation for subsequent coronal images. Coronal $T_2$-weighted FSEMS (TR/TE=1600/48 ms) images were acquired for anatomical reference. Coronal planes were oriented using the kidneys as a frame of reference, while placing the read dimension along the x-axis to minimize breathing artifacts. 3D spoiled gradient echo images (GE3D) were acquired (TR/TE of 25/2.4 ms) with a field of view (FOV) of 40×90 mm$^2$ and an in-plane resolution of 156×352 µm$^2$, and a 0.94 mm slice thickness, with a flip angle of 90° in order get better contrast with higher concentrations of CA. (Young M R, Ileva L V, Bernardo M, Riffle L A, Jones Y L, Kim Y S, et al. Monitoring of tumor promotion and progression in a mouse model of inflammation-induced colon cancer with magnetic resonance colonography. NEOPLASIA. 2009; 11(3):237-46, 1p following 46. PMCID: 2647726; Fram E K, Herfkens R J, Johnson G A, Glover G H, Karis J P, Shimakawa A, et al. Rapid calculation of T1 using variable flip angle gradient refocused imaging. MAGNETIC RESONANCE IMAGING. 1987; 5(3):201-8).

A total of 4 averages were acquired with a total scan time of 7 minutes. MRI contrast agent was administered orally via gavage for contrast enhanced MRI experiments. Post-contrast experiments were initiated immediately following gavage to include the time-points: 0.5, 2.5, 3.3, 6.5, 7.7, 16.7, 24.3, 27.5, and 46 hours. Spin-lattice relaxation experiments were performed using PS, with multiple TR values of: 5, 1.87, 0.7, 0.26, and 0.098 seconds. A 2D spin echo experiment was used (SEMS) with a FOV of 45×90 mm$^2$ and an in-plane resolution of 176×352 µm$^2$ and a slice thickness of 1.2 mm.

Figure 10:
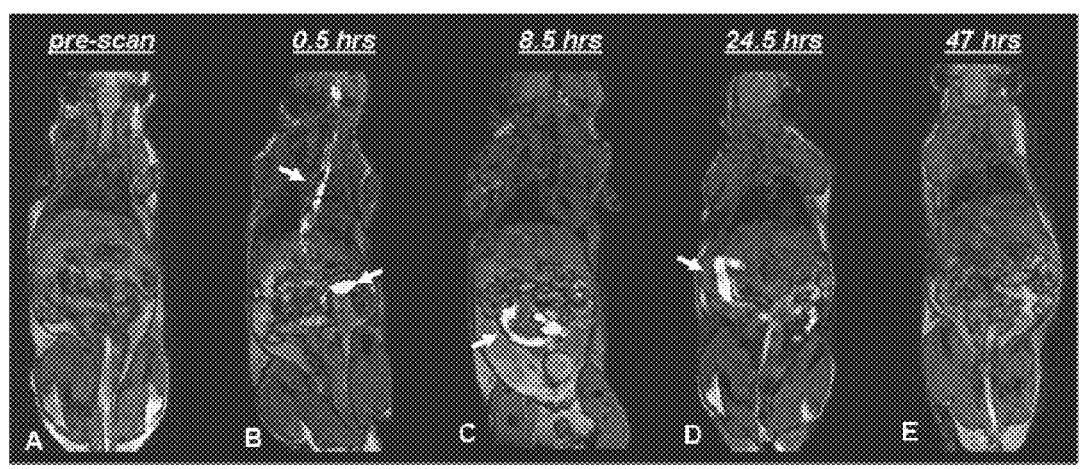
FIG. 10A-E is a series of MRI images depicting Gd-DOTA-sucrose-8 contrast agent passing through C3H mouse GI tract at various timepoints. (A) pre-scan; (B) At 0.5 h post-gavage, bright contrast is observed in the esophagus and stomach; (C) at 8.5 h contrast is observed in the small intestine; (D) at 24.5 h contrast is observed in the large intestine; and (E) by 47 h all contrast has cleared the GI tract. Arrows indicate points of bright CA-related contrast.

The single-Gd compound had low solubility in aqueous solution, low in vitro phantom relaxivity values and was not detected in vivo at any concentration. However, after orally introducing 0.5 mL of 2.5 mM 6.5-Gd compound by gavage, high contrast to noise ratio in vivo was observed (>100). This enhancement was maintained throughout passage through the gut, and the agent was observed to clear through the GI tract over a time course of 48 h (FIG. 10).

CT Contrast Using Gold Nanoparticles

For CT contrast, Iodine and Barium compounds are routinely used clinically. Gold nanoparticles have recently been demonstrated to generate 88% to 115% CT contrast enhancement at both low and high tube potentials, respectively, compared to iopromide, a commercial iodine-based CT contrast agent. (Jackson P A, Abd Rahman W N W, Wong C J, Ackerly T, Geso M. Potential dependent superiority of gold nanoparticles in comparison to iodinated contrast agents. European Journal of Radiology. 2010; 75(1): 104-9). In addition, iodinated agents are known to be associated with certain risks, especially in patients with impaired renal function. (Lang E K, Foreman J, Schlegel J U, Leslie C, List A, Mccormick P. The Incidence of Contrast-Medium Induced Acute Tubular-Necrosis Following Arteriography—a Preliminary-Report. Radiology. 1981; 138(1):203-6; Morcos S K, Thomsen H S. Adverse reactions to iodinated contrast media. European Radiology. 2001; 11(7):1267-75; Namasivayam S, Kalra M K, Torres W E, Small W C. Adverse reactions to intravenous iodinated contrast media: an update. Curr Probl Diagn Radiol. 2006; 35(4):164-9). Gold nanoparticles are attractive for many reasons including: prevalent use of gold-based compounds in medicine such as chrysotherapy. (Eisler R. Chrysotherapy: a synoptic review. Inflammation Research. 2003; 52(12):487-501). Advantages include their benign toxicity profile, and well established bio-conjugation strategies that permit conjugation of specific ligands, peptides and antibodies. (Murphy C J, Gole A M, Stone J W, Sisco P N, Alkilany A M, Goldsmith E C, et al. Gold Nanoparticles in Biology: Beyond Toxicity to Cellular Imaging. Accounts of Chemical Research. 2008; 41(12):1721-30; Chen Y S, Hung Y C, Liau I, Huang G S. Assessment of the In Vivo Toxicity of Gold Nanoparticles. Nanoscale Research Letters. 2009; 4(8):858-64; Boisselier E, Astruc D. Gold nanoparticles in nanomedicine: preparations, imaging, diagnostics, therapies and toxicity. Chemical Society Reviews. 2009; 38(6):1759-82; Eck W, Craig G, Sigdel A, Ritter G, Old U, Tang L, et al. PEGylated Gold Nanoparticles Conjugated to Monoclonal F19 Antibodies as Targeted Labeling Agents for Human Pancreatic Carcinoma Tissue. Acs Nano. 2008; 2(11):2263-72; Huang X H, Jain P K, El-Sayed I H, El-Sayed M A. Gold nanoparticles: interesting optical properties and recent applications in cancer diagnostic and therapy. Nanomedicine.

2007; 2(5):681-93; Pissuwan D, Cortie C H, Valenzuela S M, Cortie M B. Gold nanosphere-antibody conjugates for hyperthermal therapeutic applications. Gold Bulletin. 2007; 40(2):121-9). Ongoing clinical trials using gold nanoparticles have also paved the way for their use for clinical applications. (Cole J R, Mirin N A, Knight M W, Goodrich G P, Halas N J. Photothermal Efficiencies of Nanoshells and Nanorods for Clinical Therapeutic Applications. Journal of Physical Chemistry. 2009; 113(28): 12090-4)

Figure 11:
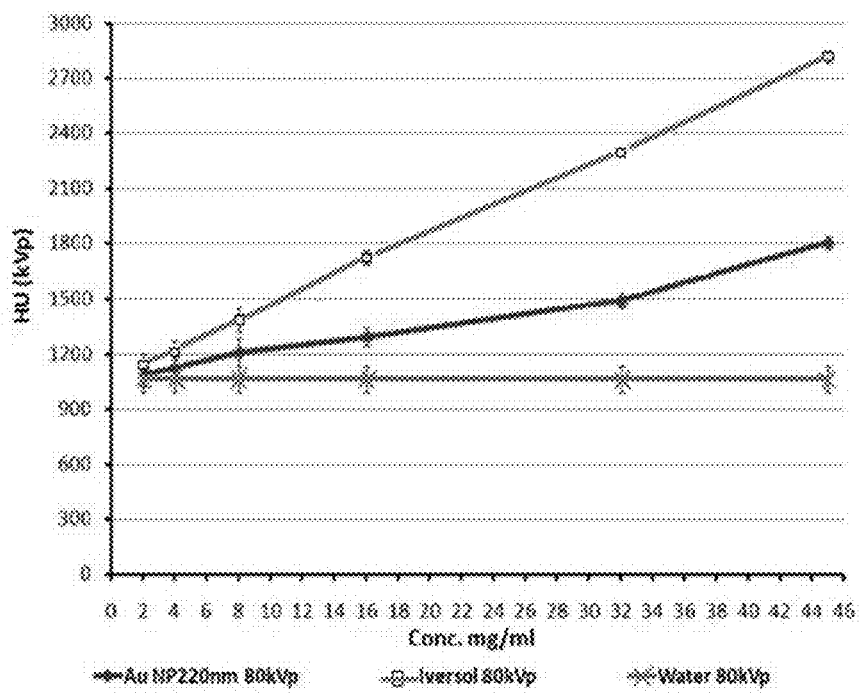
FIG. 11 is a graph depicting clinical CT measurements (80 kVp) of 220 nm gold nanoparticles suspended in agarose (dark grey) and Iversol (light grey) at a range of concentrations. Water (medium grey) was measured as a control.

Using a clinical Philips Brilliance 64, the inventors evaluated gold nanoparticles in a phantom containing 3 mm diameter NMR tubes. The initial phantom was built using acrylic with a nominal density of 1.16 gm/cc with 3 mm glass tubes inserted into holes in the phantom. The phantom was imaged using 0.625 mm slices and 80, 120, and 140 KVp. The images were then analyzed using a Philips Pinnacle workstation and the HUs determined by creating a VOI for each vial and using standard analysis tools. As shown in FIG. 11, the gold particles were detectable above background signal at a concentration of 8 mg/ml. A second phantom constructed out of solid polystyrene may be used since the polystyrene has an electron density that is similar to muscle.

Her-2 targeted, 15 nm, gold nanoparticles (Nanoprobes, Inc., Yaphank, N.Y.) have been studied by μCT following intravenous injection in mice. (Hainfeld J F, O'Connor M J, Dilmanian F A, Slatkin D N, Adams D J, Smilowitz H M. Micro-CT enables microlocalisation and quantification of Her2-targeted gold nanoparticles within tumour regions. Br J Radiol. 2011; 84(1002):526-33). Dosages as high as 1 g/kg were delivered and contrast observed at the periphery of Her-2 expressing tumor xenografts. Sensitivity of detection by 70 keV μCT was estimated to be 0.5 mg/ml. However this determination was based on an extrapolation of the μCT data and ignored the differences in the effects of the image reconstruction. Image reconstruction on actual patients is designed for rapid review by radiologists and not for the most accurate density measurements. The inventors use clinical imaging techniques to determine a more realistic sensitivity for detecting the Au nanoparticles in humans.

MRI CA Development

Modified formulations of the Gd-sucrose scaffold described above may be made to adjust the number of Gd(III) chelates attached to deliver optimal contrast and for attachment of the targeting ligands. The overall stability of the Gd-sucrose CA formulations is determined as a function of pH, temperature, detergent action of bile salts, and catalytic digestion.

CT CA Development

Although Nanogold particles may be purchased with functional groups attached, it is beneficial to have different ligand-loading schemes. Both sizes of particles, 1.6 nm and 6 nm diameter, are used to determine the effect of size on limits of detection. The overall stability of the Au nanoparticle formulations is determined as a function of pH, temperature, detergent action of bile salts and catalytic digestion.

MRI Studies

As described above, each MRI CA formulation may be evaluated in vitro and in vivo to determine the T1 relaxivity, fold-enhancement and the in vivo molar limits of detection. Agent conspicuity may be compared to Magnavist, a Gd containing contrast agent in clinical use. For in vitro experiments, phantom samples may be prepared in different dilutions of CA. $T_1$ is determined by inversion-recovery, the $T_2$ by spin-echo and the $T_2^*$ by gradient echo imaging to determine $R_1$, $R_2$ and $R_2^*$ for each reagent. MR experiments may be performed at 1.5 and 7.0 Tesla on clinical and animal scanners, respectively. From these data the relative detectability of each reagent is predicted, and 2-3 formulations may be chosen for in vivo targeting studies.

For in vivo experiments, 0.5 ml of contrast sample is introduced into the stomach by gavage. In vivo sample sizes are determined by power analysis using representative data from previous comparable imaging studies. From these data, the minimum volume and concentration required for detection is determined for each formulation. Acquisitions are reconstructed into 3D images for better visualization and are evaluated by a radiologist for potential clinical utility. New formulations are evaluated throughout the study to identify an optimal CA that can detect lesions of ~1 mm in diameter. Despite the differences in field strength, the increased voxel size of the clinical instrumentation provides an estimated 8-10 fold higher sensitivity compared to the small animal imaging system.

CT Studies

The CT conspicuity of Au nanoparticles is empirically assessed. Biostabilized Nanogold nanoparticles (Nanoprobes, Inc.) in two different sizes (1.6 nm and 6 nm diameters) are used. The number of Au atoms in each particle is known, thus the limits of detection are determined in terms of molar Au concentration. Particle conspicuity is compared to Gastrografin®. Particles are resuspended at various concentrations and added to the wells of a polystyrene phantom. The goal for detection is 1 mm in diameter and 0.5 mm in depth since the malignant risk of colon polyps is size dependent. It is known that lesions smaller than 1 mm diameter rarely display high grade dysplasia, and flat adenomas can have a depth as thin as 0.5 mm. (Lau P C, Sung J J. Flat adenoma in colon: two decades of debate. J Dig Dis. 2010; 11(4):201-7).

To study the limits of detection a solid polystyrene phantom is constructed containing volumes ranging from about 1 mm to about 4 mm in diameter and with depths of about 0.5 mm to about 4 mm. The phantom reflects the clinical situation with a colon that has been prepped. The situation of no colon prep is mimicked by sandwiching the basic phantom between two additional sheets of polystyrene. In the original phantom study (FIG. 11), mouse feces were suspended in water evaluated for relative absorptivity in HU, and no statistical difference was observed in absorptivity compared to water alone. A range of Au concentrations based on the number of gold atoms in solution is used and the limits of detection are studied at a range of energy levels in both clinical CT systems and the Inveon μCT system by Siemens. Limits of detection are studied in C3H mice following oral administration by gavage. Concentrations are determined in vivo by molar HUs and these data are analyzed in the Biostatistics and Bioinformatics Core to determine the in vivo limits of detection. As above for MRI, the study radiologist evaluates these data for clinical utility.

For each mouse and CA construct, at least 4 different concentration levels are examined to determine the limit of detection. The limit of detection for MRI is defined as relative enhancement, i.e. tumor signal—healthy tissue signal/healthy tissue signal, or as otherwise stated, a signal that is greater than the surrounding unaffected tissue. The contrast agent concentration for a given ROI can be determined by the relaxation rate (R1) and the previously determined relaxivity (r1). A simple linear regression is utilized to estimate the limit of detection, with the concentration and the relative enhancement being the exploratory and response variable, respectively. A total of 5 mice are evaluated. The relative enhancement is highly correlated with the concentration. A total of 20 data points (5 mice×4 concentration levels) provides 91% power to detect a difference of about 0.65 between the null correlation of 0 and the alternative correlation of 0.65 at 5% significance level. For the CT study, the limit of detection is defined as the minimal Au concentration at which molar HU values are significantly different from water (or normal tissue) HU values. To this end, one-sided paired t-test is used to detect the difference at 5% significance level with no multiplicity adjustment. A total of 5 mice provide 91% power to detect an effect size of about 2.0 at 5% significance level using one-sided t-test.

EXAMPLE 3

Development of CRC-Targeted Molecular Imaging Probes Using TLR4-Specific Ligands High-affinity binding ligands are available for Toll-like receptor 4 (TLR4), including the synthetic lipid A derivative, Eritoran; an irreversible inhibitor, TAK 242; and β-amino alcohol-type inhibitors. These ligands are individually evaluated for binding activity and selectivity using TLR4-expressing HT-29 cells and non-expressing tumor cell lines and the existing in cyto binding assay. The ligand with the highest affinity and specificity for TLR4 is tested for biostability at 37° C. and low pH. The ligand may also be tested in serum prior to attachment to existing MRI and CT contrast agents to form highly selective multivalent binding constructs. A gold nanoparticle formulation and a sucrose-based scaffold carrying multiple DOTA-Gd(III) chelates is used for in vivo µCT and MRI in mice. Agonist/antagonist activity of the targeted contrast agents is determined using a bioassay for NF-κB signaling through TLR4 that was previously developed. Binding avidity of the multivalent constructs is determined Formulations with high avidities are orally delivered by gavage to mice and imaged in vivo and ex vivo by µCT or MRI using an orthotopic xenograft model of colon tumor cells surgically implanted into the colon. Biostability is evaluated as described previously in Example 2.

Fresh colon polyps and tumors removed from patients are stained with the probe ex vivo prior to fixation then imaged, fixed and IHC stained for marker expression. Image intensity values are statistically correlated to IHC staining levels.

As illustrated in Example 1, the inventors have discovered CRC-specific cell surface markers. Using available DNA microarray data from patient tissue samples for gene expression profiling, cell surface targets were identified that distinguish colon adenomas and adenocarcinomas from normal tissues in the GI tract including CLDN1, LY6G6D and TLR4 (FIG. 2). By gene expression profiling, at least one of two markers, TLR4 or CLDN1, are expressed in 100% of adenocarcinomas and adenomas surveyed. Protein expression was confirmed for CLDN1, LY6G6D and TLR4 by IHC of patient samples in a CRC tissue microarray (Table 6).

TABLE 6

IHC scoring of CRC markers

| Target | Tissue type | Patient Tissue Samples (n) | 0 | 1 | 2 | 3 | 4 | 6 | 9 | % ≥ 4 |
|---|---|---|---|---|---|---|---|---|---|---|
| CLDN1 | Normal | 25 | 1 | 1 | 8 | 15 | 0 | 0 | 0 | 0 |
|  | Adenoma | 24 | 1 | 0 | 0 | 4 | 0 | 15 | 4 | 79 |
|  | Adenocarcinoma | 80 | 0 | 0 | 6 | 20 | 8 | 28 | 18 | 68 |
| LY6G6D | Normal | 13 | 0 | 0 | 0 | 7 | 0 | 6 | 0 | 46 |
|  | Adenoma | 16 | 0 | 0 | 0 | 2 | 2 | 6 | 6 | 88 |
|  | Adenocarcinoma | 57 | 0 | 0 | 9 | 16 | 1 | 19 | 12 | 56 |
| TLR4 | Normal | 15 | 0 | 0 | 11 | 3 | 0 | 0 | 1 | 7 |
|  | Adenoma | 16 | 0 | 0 | 2 | 4 | 0 | 8 | 2 | 63 |
|  | Adenocarcinoma | 60 | 2 | 0 | 16 | 15 | 1 | 20 | 6 | 45 |

FIG. 4 shows representative IHC staining for these three markers. CLDN1 is highly expressed (pathology score≥4) as protein in 79% of adenomas (n=24) and 68% of adenocarcinomas (n=80), and is not expressed in normal colon samples, 0% (n=25) at that level. TLR4 is highly expressed in 63% of adenomas (n=16) and 45% of adenocarcinoma (n=60), and is expressed in only 7% of "normal" samples (which include adjacent normal). LY6G6D is expressed in a high percentage of adenomas (88%) and adenocarcinomas (56%), but was also observed in an unacceptably high number (46%) of normal samples. TLR4 or CLDN1 stained≥4 in 83% of adenoma and adenocarcinoma cores in the CRC TMA (Table 7).

TABLE 7

Coverage by IHC staining ≥4.

| Marker | # of cores | Coverage |
|---|---|---|
| CLDN1 | 52/72 | 72% |
| TLR4 | 36/72 | 50% |
| CLDN1 + TLR4 | 60/72 | 83% |

Figure 12:
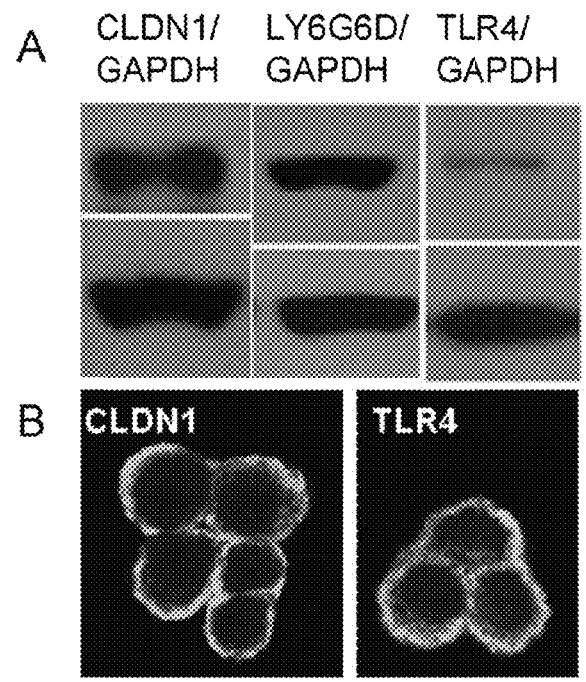
FIG. 12A-B is a series of images depicting that protein expression was confirmed in HT-29 colon tumor cells by A) Western blot for CLDN1, LY6G6D and TLR4, GAPDH (bottom panel) as loading control; and B) immunocytochemistry for CLDN1 and TLR4, green staining represents marker expression, plasma membrane is stained red (WGA) and nucleus is stained blue (DAPI).

CRC tumor cell lines expressing TLR4 have been identified. Based on DNA microarray data for 26 CRC tumor cell lines, 9 cell lines were selected to characterize expression and non-expression of these markers by qRT-PCR, Western blot and immunocytochemistry (ICC). The HT-29 cell line was found to express CLDN1, LY6G6D and TLR4 as protein (FIG. 12A). To confirm cell-surface expression, ICC was performed for TLR4 and CLDN1 (FIG. 12B).

Toll-like receptor 4 (TLR4) is a member of the toll-like receptor gene family. TLR4 is a cell-surface protein that typically functions in the immune system surveillance of bacterial infection by recognizing components of the bacterial cell membrane. However, TLR4 is reported to be overexpressed in CRC. (Cammarota R, Bertolini V, Pennesi G, Bucci E O, Gottardi O, Garlanda C, et al. The tumor microenvironment of colorectal cancer: stromal TLR-4 expression as a potential prognostic marker. J Transl Med. 2010; 8:112. PMCID: 2997091). Binding ligands are available for TLR4 including lipopolysaccharides derived from lipid A, the TLR4 selective inhibitor TAK 242, β-amino alcohol inhibitors, Besifloxacin and a number of decoy peptides derived from interacting proteins.

Synthetic lipid A is available in pure form (MPLA-S). However, it has a complicated structure with limited options for attachment and has high hydrophobicity which limits the potential for use of MPLA-S in multimerization and attachment of fluorescent dye. Perhaps a better lipid A derivative is found in Eritoran (Eisai Co.), an investigational drug for the treatment of severe sepsis. It is administered intravenously as eritoran tetrasodium and is in a Phase III trial (ClinicalTrials.gov NCT00334828 ACCESS: A Controlled Comparison of Eritoran Tetrasodium and Placebo in Patients with Severe Sepsis). Eritoran has lower lipophilicity compared to lipid A due to the removal of methylene groups (lipid A has 84 and Eritoran has only 52 methylenes) and the addition of a phosphate group (two phosphates total).

Alternatively, two types of small molecule TLR4 inhibitors are available, TAK 242 and β-amino alcohols. (Ii M, Matsunaga N, Hazeki K, Nakamura K, Takashima K, Seya T, et al. A novel cyclohexene derivative, ethyl (6R)-6-[N-(2-Chloro-4-fluorophenyl)sulfamoyl]cyclohex-1-ene-1-carboxylate (TAK-242), selectively inhibits toll-like receptor 4-mediated cytokine production through suppression of intracellular signaling. Mol Pharmacol. 2006; 69(4):1288-95; Chavez S A, Martinko A J, Lau C, Pham M N, Cheng K, Bevan D E, et al. Development of beta-amino alcohol derivatives that inhibit Toll-like receptor 4 mediated inflammatory response as potential antiseptics. J Med Chem. 2011; 54(13):4659-69. PMCID: 3131463; Bevan D E, Martinko A J, Loram L C, Stahl J A, Taylor F R, Joshee S, et al. Selection, Preparation, and Evaluation of Small-Molecule Inhibitors of Toll-Like Receptor 4. ACS Med Chem Left. 2010; 1(5):194-8. PMCID: 2930797). Both inhibitors have known structure-activity relationships (SAR) with potential for multivalent attachment. (Bevan D E, Martinko A J, Loram L C, Stahl J A, Taylor F R, Joshee S, et al. Selection, Preparation, and Evaluation of Small-Molecule Inhibitors of Toll-Like Receptor 4. ACS Med Chem Left. 2010; 1(5):194-8. PMCID: 2930797; Yamada M, Ichikawa T, Ii M, Sunamoto M, Itoh K, Tamura N, et al. Discovery of novel and potent small-molecule inhibitors of NO and cytokine production as antisepsis agents: synthesis and biological activity of alkyl 6-(N-substituted sulfamoyl)cyclohex-1-ene-1-carboxylate. J Med Chem. 2005; 48(23):7457-67). The TAK 242 inhibitor has low nanomolar inhibition ($IC_{50}$=3.2 nM) and has advanced to phase III clinical trials for sepsis. The best of the β-amino alcohols possess much lower inhibition activity, $IC_{50}$ 17 μM. However, if these low affinity ligands have high TLR4 selectivity, multivalent constructs using these ligands could lead to high overall avidity and high selectivity. (Brabez N, Lynch R M, Xu L, Gillies R J, Chassaing G, Lavielle S, et al. Design, synthesis, and biological studies of efficient multivalent melanotropin ligands: tools toward melanoma diagnosis and treatment. J Med Chem. 2011; 54(20):7375-84). However, as antagonists, it is possible that binding does not lead to internalization. Internalization of CAs is of potential importance as it will increase the longevity of contrast and amplify the signal.

TLR activity bioassays were developed previously for TLR2. The inventors previously used an NF-κB promoter-mediated luminescence bioassay using TLR2+/−cells (HEK293-TLR2 and parental HEK293), known TLR2 agonists (Pam2CSK4 and Pam3CSK4) as controls and a vector (pNiFty-Luc) containing luciferase under the control of the NF-κB promoter (all purchased from InvivoGen, San Diego, Calif.). In previous work, the inventors identified TLR2 as an important target for pancreatic cancers. (Morse D L, Balagurunathan Y, Hostetter G, Trissal M, Tafreshi N K, Burke N, et al. Identification of novel pancreatic adenocarcinoma cell-surface targets by gene expression profiling and tissue microarray. Biochem Pharmacol. 2010; 80(5):748-54. PMCID: 2914681). Following transient transfection with the vector, cells are treated with test samples and luciferase expression determined by addition of luciferin and acquiring luminescence measurements using our Victor X4 2030 multilabel plate-reader (Perkin-Elmer). The agonist assay compares the NF-κB mediated luminescence activation by the test agent compared to activation by control agonist. The assay can also be used to characterize antagonists by using an excess of test agent combined with increasing concentrations of unconjugated ligand. The above bioassays can be applied equally to TLR4 ligand through the use of TLR4 ligand (MPLA-S) and expressing cells (HEK-293-TLR4/MD-2/CD14) (InvivoGen, San Diego, Calif.).

Cell Lines and Tumor Model

For evaluation of ligand bioactivity, the inventors use HEK293-TLR4 and parental HEK293 cells (InvivoGen). For binding assays, HT-29 colon cancer cells is used since there is high constitutive expression of TLR4 by qRT-PCR, Western blot and immunocytochemistry (ICC) (FIG. 4). For in vivo testing, an orthotopic xenograft model of CT-26 cells surgically implanted into the colon of BALB/c mice has been developed. (Shi H, Xu J M, Hu N Z, Wang X L, Mei Q, Song Y L. Transfection of mouse macrophage metalloelastase gene into murine CT-26 colon cancer cells suppresses orthotopic tumor growth, angiogenesis and vascular endothelial growth factor expression. Cancer Left. 2006; 233(1):139-50; Chen Y, Chang K J, Hwang L H, Chen C N, Tseng S H. Establishment and characterization of a rectal cancer model in mice: application to cytokine gene therapy. Int J Colorectal Dis. 2002; 17(6):388-95). This model may be recapitulated using HT-29 cells. For in vivo tumor selectivity experiments following intravenous injection, bilateral (+/−) flank subcutaneous tumors in mice is used. Positive and negative expressing tumor lines are engineered using a TLR4 non-expressing parental tumor line and the pUNO-hTLR4A and PDUO2-hMD2/CD14 expression vector (InvivoGen).

Evaluation and Characterization of TLR4 Ligands.

Eritoran, TAK 242 and the most promising TLR4 selective β-amino alcohol inhibitor is evaluated for bioactivity using the TLR activity assay described above. In order to track synthetic material by MS/MS ex vivo, select heavy ($^{13}$C and $^{2}$H) amino acids are used. Biostability of ligands is determined at 37° C. in the presence of low pH or serum, and MS/MS is used to detect degradation. Eu-DTPA is attached to each ligand and re-valuated to assure that bioactivity has not been altered. If necessary, a number of attachment sites and linker lengths are systematically screened to identify the optimal configuration. Binding (Kd) is determined by time-resolved fluorescence (TRF) saturation binding assay using the Victor X4 2030 multilabel plate-reader (Perkin-Elmer) and ligand variations and multivalent targeted CA constructs are evaluated for binding affinity or avidity (Ki) by our established TRF competitive binding assay. (Handl H L, Vagner J, Yamamura H I, Hruby V J, Gillies R J. Lanthanide-based time-resolved fluorescence of in cyto ligand-receptor interactions. Analytical Biochemistry. 2004; 330(2):242-50; Vagner J, Xu L, Handl H L, Josan J S, Morse D L, Mash E A, et al. Heterobivalent ligands crosslink multiple cell-surface receptors: the human melanocortin-4 and delta-opioid receptors. Angew Chem Int Ed Engl. 2008; 47(9): 1685-8; Xu L, Vagner J, Josan J, Lynch R M, Morse D L, Baggett B, et al Enhanced targeting with heterobivalent ligands. Mol Cancer Ther. 2009; 8(8):2356-65; Barkey N M, Tafreshi N K, Josan J S, De Silva C R, Sill K N, Hruby V J, et al. Development of Melanoma-Targeted Polymer Micelles by Conjugation of a Melanocortin 1 Receptor (MC1R) Specific Ligand. J Med Chem. 2011; 54(23):8078-84; Rao V, Alleti R, Xu L, Tafreshi N K, Morse D L, Gillies R J, et al. A sucrose-derived scaffold for multimerization of bioactive peptides. Bioorg Med Chem. 2011; 19(21):6474-82. PMCID: 3197697). Graph Pad Prism non-linear regression analysis software is used to calculate the binding constants from the resulting assay data.

Development of Targeted MRI CA

Various numbers of promising ligands identified above are attached to the Gd-sucrose scaffold, described previously, and relative binding avidities are evaluated while maintaining maximum Gd(III) loading of the agent. Versions with one-, two- and three-ligand attachments for bioactivity and binding avidity are evaluated using the bioassay and TRF competitive binding assays described above. Since TLR2 is potentially cross-reactive with TLR4 ligands, TLR4 specificity is determined by performing the same assays using the established TLR2 bioactivity and binding assays. This is similar to work the inventors have performed previously to develop a MC1R (melanocortin-1 receptor) specific ligand following multimerization onto a nanoagent construct.

Development of Targeted CT CA

Biocompatible and stable Nanogold nanoparticles (Nanoprobes, Inc.) are purchased with functional groups for attachment. Versions with maleimide, thiol and amine functional groups are available. A thiol is added to the ligand for attachment to maleimide functionalized nanoparticles. An alternative approach is to use Cu-free azide/cyclooctyne coupling. (Jewett J C, Bertozzi C R. Cu-free click cycloaddition reactions in chemical biology. Chem Soc Rev. 2010; 39(4):1272-9. PMCID: 2865253; Kuzmin A, Poloukhtine A, Wolfert M A, Popik V V. Surface functionalization using catalyst-free azide-alkyne cycloaddition. Bioconjug Chem. 2010; 21(11):2076-85). These particles are readily available in 1.6 nm and 6 nm diameters. Six nm particles are evaluated and ligands are conjugated to the Au particles and the formulated constructs are purified. Ligand loading conditions are varied to determine the conditions leading to maximum binding and activity. Constructs are tested for bioactivity and binding as described above. Nanoprobes can be built for particles of larger dimensions.

MRI Studies

Targeted agents having the highest binding avidity and TLR4 specificity are used in phantom relaxation experiments to determine molar relaxivity. In vivo gavage experiments, as described previously, include groups of control BALB/c mice with no xenograft and mice bearing HT-29 colon xenografts. Agents are delivered by gavage and imaged over a 48 h time-course.

CT Studies

The Nanogold agents developed above based on binding avidity and TLR4 selectivity are used as described in Example 2. Phantoms containing these constructs are assessed in both the clinical Philips Brilliance 64 system and the Seimens Inveon small animal CT system to determine the molar limits of detection in HUs. As described above for MRI, in vivo experiments include groups of control BALB/c mice with no xenograft and mice bearing HT-29 colon xenografts. Images are acquired over a time-course following gavage.

All xenografts used in the above imaging studies, and organs used for ex vivo imaging are removed immediately following the last imaging time-point, fixed and sent to pathology for embedding, sectioning and IHC staining to determine TLR4 expression. Xenograft tumor samples are deposited in the Tissue and Data Core.

Clinical Studies

The MRI and CT formulations developed above are tested using fresh adenoma and adenocarcinoma tissues directly from patients. Fresh polyp samples and an adjacent normal biopsy sample are delivered to a pathologist where the polyp is sectioned into two pieces. Fresh tumor samples may also be delivered to the gross room from the surgeon where it will be sectioned into two pieces and an adjacent normal biopsy sample is also collected. One piece is retained by pathology to undergo standard examination. The other half and the corresponding adjacent normal sample are placed in buffer containing the imaging probe and incubated for 15 mins followed by 3 washes in ice cold buffer. Then, ex vivo images are acquired immediately using the small animal CT or MRI instruments Immediately after imaging, samples are placed in fixative and returned to pathology for examination.

From time of collection to fixation, the samples are kept on ice and the duration is no longer than 2 h. The face of the sample retained in pathology immediately adjacent to the section that was removed for imaging is sectioned and IHC stained for TLR4 expression. The adjacent normal sample is mounted on the same slide and stained together with the CRC section. IHC stained slides are scanned in the Moffitt Analytic Microscopy Core using the Aperio™ (Vista, Calif.) ScanScope XT with a 200×/0.8NA objective lens at a rate of 2 minutes per slide via Basler tri-linear-array Immunopositivity of biomarkers within the nucleus, cytoplasm and membrane of cells of interest are quantitatively scored with regard to the percent positivity and the intensity using TissueStudio v3.0 (Definiens, Munich, Germany). Quantified IHC values are correlated with ex vivo image values obtained for the corresponding sample. Once the samples used for imaging are examined by pathology, they are deposited in the Tissue and Data Core.

For CT and MRI studies, the same methods applied to Example 2 are used to determine the limits of detection, and 5 mice are examined for each study. For the clinical study, the Spearman method is used to estimate the correlation between IHC intensity and probe image intensity. For each tissue type (adenoma and adenocarcinoma), a sample size of 30 will provide 83% power to detect a difference of 0.5 between the null correlation of 0 and the alternative correlation of 0.5 at two-sided 5% significance level.

EXAMPLE 4

Ligand Development for Additional CRC Markers

Peptidomimetic binding ligands with high biostability and specificity for the validated marker CLDN1 are developed. Together, TLR4 and CLDN1 are highly expressed in 83% of CRC by protein (IHC) and 100% by mRNA expression. Ligands are developed via rational design, high-throughput library synthesis and screening by binding assay and one-bead one-compound cell-adhesion assay. Hits are iteratively improved using gained structure activity relationships (SAR) to develop follow-up libraries until lead high affinity compounds are discovered. Lead compounds are tested for stability as described in Example 2. IHC validation of protein expression for additional CRC markers is performed with the goal of identifying markers that provide 100% coverage of colon adenomas and adenocarcinomas. Patient data is analyzed retrospectively to determine the prognostic value of validated markers.

CLDN1 has Known SAR

As stated previously, claudins form a large gene family (at least 24 members) involved in formation of tight-junctions. (Deli M A. Potential use of tight junction modulators to reversibly open membranous barriers and improve drug delivery. Biochim Biophys Acta. 2009; 1788(4):892-910). Claudins form homo- and hetero-dimers via 2 extracellular domains (ECD1&2). (Krause G, Winkler L, Mueller S L, Haseloff R F, Piontek J, Blasig I E. Structure and function of claudins. Biochim Biophys Acta. 2008; 1778(3):631-45). CLDN1 does not have a known ligand. However, ligands have been developed for CLDN4 from the N-terminal 16 to 30 amino acids and these ligands have been found to interact with ECD2 of CLDN4. (Masuyama A, Kondoh M, Seguchi H, Takahashi A, Harada M, Fujii M, et al. Role of N-terminal amino acids in the absorption-enhancing effects of the c-terminal fragment of *Clostridium perfringens* enterotoxin. J Pharmacol Exp Ther. 2005; 314(2):789-95; Takahashi A, Kondoh M, Masuyama A, Fujii M, Mizuguchi H, Horiguchi Y, et al. Role of C-terminal regions of the C-terminal fragment of *Clostridium perfringens* enterotoxin in its interaction with claudin-4. J Control Release. 2005; 108(1):56-62). A 27-mer peptide derived from the second half of the first domain of Claudin 1 ($CLDN1_{53-80}$) is known to reversibly interfere with tight junction structure and function, strongly associate with the plasma membrane, and interact with CLDN1 and occludin. The native 27-mer contains a cysteine that is not important for activity and can be replaced with serine or used as a thiol attachment point. Smaller overlapping peptide fragments failed to interact, but a definitive study with carefully designed overlapping peptides has yet to be conducted. (Mrsny R J, Brown G T, Gerner-Smidt K, Buret A G, Meddings J B, Quan C, et al. A key claudin extracellular loop domain is critical for epithelial barrier integrity. Am J Pathol. 2008; 172(4):905-15. PMCID: 2276422).

Rational Design and High-throughput Synthesis of Soluble Peptidomimetic Libraries.

A longstanding focus of the Ligand Discovery Laboratory (LDL) is the design and development of peptidomimetic compounds for in vivo pharmacologic applications. (Hruby V J, Balse P M. Conformational and topographical considerations in designing agonist peptidomimetics from peptide leads. Curr Med Chem. 2000; 7(9):945-70; Hruby V J. Designing peptide receptor agonists and antagonists. Nat Rev Drug Discov. 2002; 1(11):847-58; Hruby V J, Qui W, Okayama T, Soloshonok V A. Design of nonpeptides from peptide ligands for peptide receptors. Methods Enzymol. 2002; 343:91-123; Cowell S M, Gu X, Vagner J, Hruby V J. Intelligent design in combinatorial chemistry: use of designed peptide libraries to explore secondary and tertiary structures in peptides and proteins. Methods Enzymol. 2003; 369:288-97; Vagner J, Qu H, Hruby V J. Peptidomimetics, a synthetic tool of drug discovery. Curr Opin Chem Biol. 2008; 12(3):292-6. PMCID: 2515564; Yamamoto T, Nair P, Jacobsen N E, Vagner J, Kulkarni V, Davis P, et al. Improving metabolic stability by glycosylation: bifunctional peptide derivatives that are opioid receptor agonists and neurokinin 1 receptor antagonists. J Med Chem. 2009; 52(16):5164-75; Josan J S, Morse D L, Xu L, Trissal M, Baggett B, Davis P, et al. Solid-phase synthetic strategy and bioevaluation of a labeled delta-opioid receptor ligand Dmt-Tic-Lys for in vivo imaging. Org Left. 2009; 11(12):2479-82. PMCID: 2756606; Flynn A N, Tillu D V, Asiedu M N, Hoffman J, Vagner J, Price T J, et al. The protease-activated receptor-2-specific agonists 2-aminothiazol-4-yl-LIGRL-NH2 and 6-aminonicotinyl-LIGRL-NH2 stimulate multiple signaling pathways to induce physiological responses in vitro and in vivo. J Biol Chem. 2011; 286(21):19076-88. PMCID: 3099721; Boitano S, Flynn A N, Schulz S M, Hoffman J, Price T J, Vagner J. Potent agonists of the protease activated receptor 2 (PAR2). J Med Chem. 2011; 54(5):1308-13. PMCID: 3069554). Peptidomimetics are highly effective receptor ligands that closely resemble the natural ligands of the targeted receptor. Three broad themes from the LDL are incorporated to develop long-lived, specific agonists: 1) optimization of conformational constraints of endogenous peptides to allow for increased ligand binding; 2) conversion of peptides to peptidomimetics using synthetic scaffolds, peptide bond isosteres, or unnatural amino acids to allow for novel, stable and minimally toxic ligands for in vivo use; and 3) high throughput synthesis/screening iterative feedback to continually improve our novel agonist/antagonists. (Yamamoto T, Nair P, Ma S W, Davis P, Yamamura H I, Vanderah T W, et al. The biological activity and metabolic stability of peptidic bifunctional compounds that are opioid receptor agonists and neurokinin-1 receptor antagonists with a cystine moiety. Bioorg Med Chem. 2009; 17(20):7337-43. PMCID: 2775479; Lee Y S, Agnes R S, Cain J P, Kulkarni V, Cai M, Salibay C, et al. Opioid and melanocortin receptors: do they have overlapping pharmacophores? Biopolymers. 2008; 90(3):433-8. PMCID: 2693099; Yamamoto T, Nair P, Vagner J, Largent-Milnes T, Davis P, Ma S W, et al. A structure-activity relationship study and combinatorial synthetic approach of C-terminal modified bifunctional peptides that are delta/mu opioid receptor agonists and neurokinin 1 receptor antagonists. J Med Chem. 2008; 51(5):1369-76. PMCID: 2737825; Mayorov A V, Cai M, Palmer E S, Dedek M M, Cain J P, Van Scoy A R, et al. Structure-activity relationships of cyclic lactam analogues of alpha-melanocyte-stimulating hormone (alpha-MSH) targeting the human melanocortin-3 receptor. J Med Chem. 2008; 51(2):187-95. PMCID: 2587288; Ying J, Gu X, Cai M, Dedek M, Vagner J, Trivedi D B, et al. Design, synthesis, and biological evaluation of new cyclic melanotropin peptide analogues selective for the human melanocortin-4 receptor. J Med Chem. 2006; 49(23):6888-96. PMCID: 1764620). Importantly, these strategies have resulted in exclusive access to novel peptidomimetic scaffolds that will be incorporated into the current probe design.

Alternate Approach for Discovery of Ligands Using Random Peptide OBOC Libraries

OBOC libraries are of larger scale ($10^6$-$10^8$ compounds) and can be screened with very high-throughput (1 to $3\times10^5$ compounds per screening day), and thus are suitable for more aggressive design, including the combination of building blocks with uncertain impact. Spatially segregated beads the encoding sequence to be carried inside while the external surface, accessible to the cells, carries the mimetic library. Thus, the structure can be retrieved by determining the code sequence by mass spectrometry, which corresponds to the specific order of individual building blocks used to construct the ligand (see FIG. 13).

OBOC technology was developed at the University of Arizona by Kit Lam and Victor Hruby. (Lam K S, Salmon S E, Hersh E M, Hruby V J, Kazmierski W M, Knapp R J. A new type of synthetic peptide library for identifying ligand-binding activity. Nature. 1991; 354(6348):82-4). In this approach, synthetic compounds are built directly on polymeric solid-phase support beads by a mix-and-split approach. Libraries are generated from combinations of building blocks, which are either completely random, or alternatively, assembly can be directed if sub-structures of binding motifs are known. Small non-peptide libraries or large fabricated biopolymers require a coding strategy for the deconvolution of binding structures and for amplification of current ion signal in MS. The code defines the chemical history of any particular bead and hence the structure of the binding compound. An encoding method was used based on spatially segregated bifunctional beads with orthogonal protection groups in the external and internal regions. (Vagner J, Barany G, Lam K S, Krchnak V, Sepetov N F, Ostrem J A, et al. Enzyme-mediated spatial segregation on individual polymeric support beads: application to generation and screening of encoded combinatorial libraries. Proc Natl Acad Sci USA. 1996; 93(16):8194-9. PMCID: 38645). This procedure was developed by the inventors previously and has been improved by others. (Wang X, Peng L, Liu R, Gill S S, Lam K S. Partial alloc-deprotection approach for ladder synthesis of "one-bead one-compound" combinatorial libraries. J Comb Chem. 2005; 7(2):197-209; Liu R, Marik J, Lam K S. Design, synthesis, screening, and decoding of encoded one-bead one-compound peptidomimetic and small molecule combinatorial libraries. Methods Enzymol. 2003; 369:271-87).

Figure 13:
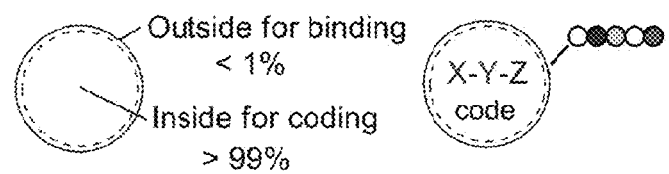
FIG. 13 is an image depicting OBOC topologically segregated bead coding technology.

Spatially segregated beads carry the encoding sequence inside while the external surface, accessible to the cells, is reserved for building blocks of the library. The code buried inside a bead and thus cannot interfere with the assay. For synthesis, solid-phase technology is employed. The binding entities are built on the surface of solid-phase resin, e.g. hydrophilic Tentagel, which is suitable for screening in aqueous buffers. As building blocks are added, e.g. block1, then block2, an internal code is simultaneously added which is buried inside the bead (FIG. 13). Protecting groups are removed from the binding structure and the library screened using the dual-color cell-adhesion-to-bead assay.

Figure 14:
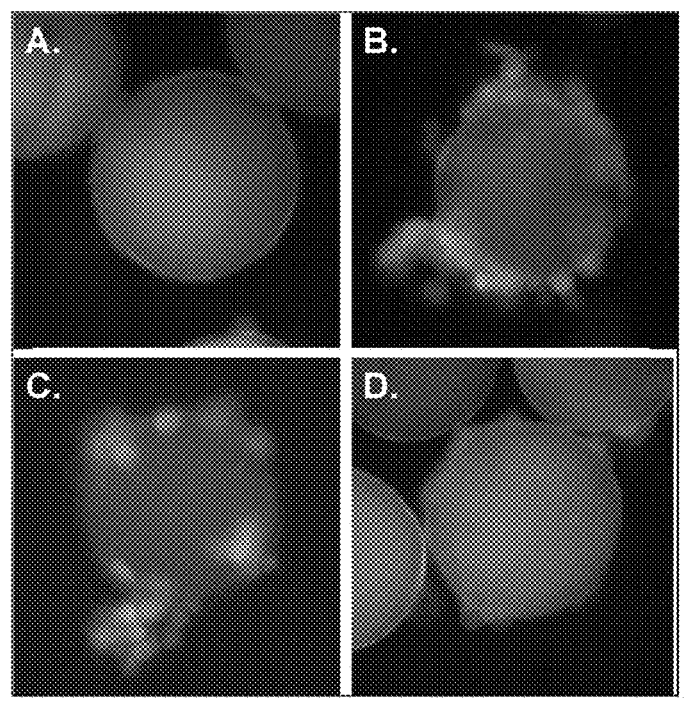
FIG. 14A-D are a series of images depicting: A) bead with no cells adhered; B) bead rosetted with both cell types; C) bead rosetted only with green positive cells (target-specific binding); and D) bead rosetted with red non-expressing cells.

The established cell-adhesion-to-bead assay is used to screen the OBOC libraries for hits. Target expressing and non-expressing control cells are labeled with Cell Tracker® Green and Cell Tracker® Orange respectively. Beads binding green cells and not orange cells contain peptides specific for the target marker (FIG. 14C), those binding only red cells are specific for an epitope expressed only on control cells (14D), whereas beads binding both green and orange cells have ligands that bind to non-specific epitopes (14B). Beads that specifically adhere to marker positive cells, but don't adhere to the non-expressing cells, are isolated using a capillary tube, treated so the internal code is cleaved from the resin, and subjected to mass-spectrometry to determine the sequence of the internal code. A small amount of code sequence (100 pmol) is adequate for about 20 MS-MS analyses. The structure of the code is specifically designed to be readily determined, with positive charge included in every residue. The structures of multiple hits are compared and evaluated to identify conserved binding motifs. Representative compounds corresponding to a consensus motif are re-synthesized, and binding is determined and improved as described above.

For binding assays, HT-29 colon cancer cells are used since the high constitutive expression of CLDN1 was determined by qRT-PCR, Western blot and immunocytochemistry (ICC).

Ligand Development and Screening

Libraries of biostable peptidomimetic ligands are produced based on the 27mer structure of $CLDN1_{53-80}$. These libraries are screened for specific binding to CLDN1 expressing HT-29 cells. First, a Eu-DTPA chelate is attached to the 27mer and binding of the resulting construct is determined using the lanthanide-based TRF saturation binding assay to determine Kd as described above in Example 3. As described in Example 3, the Eu-labeled ligand is used to determine binding of unlabeled test compounds in the libraries by TRF competitive binding assay to determine Ki. Follow-up libraries use gained SAR to iteratively develop ligands with high affinity, CLDN1 specificity and other optimal properties, e.g. reduced MW and increased solubility. As an alternate approach, random OBOC peptidomimetic libraries can be synthesized and screened using the cell-adhesion-to-bead assay described above. Ligands for additional markers are developed once CLDN1 lead compounds are established and additional markers are confirmed for protein expression in patient samples. Biostability of lead ligands is determined via MS/MS of samples treated at 37° C. and low pH or serum as described in Example 2.

IHC Validation of Additional Targets

Additional lead markers from the gene expression data are validated by IHC to provide a set of markers providing 100% coverage. At least one of the three markers TLR4, CLDN1 and LY6G6D were expressed in 97% of the tissue samples surveyed. The inventors previously identified at least 7 additional markers by gene expression profiling, including GPR56, GRM8, SLCO1B3, CLEC5A, IL1RAP, FCGR1A and OXGR1. Patient data is analyzed retrospectively to determine the prognostic value of all validated markers, including TLR4, CLDN1 and LY6G6D by correlating marker expression with therapy response and survival. Corresponding patient data is provided for tissue microarray samples that have high expression of each marker. These data are compiled in a database to determine significant correlations of marker expression with patient outcomes.

Statistical Considerations

Subjects' characteristics are summarized using descriptive statistics including mean, median, standard deviation and range for continuous measures and frequencies and proportions for categorical measures. For each marker, subjects are dichotomized by the pathology score; high (score≥4) and low (score≤3) group, and the association with response (complete or partial response vs. others) and survival is assessed by a logistic regression model and the Cox proportional hazards model, respectively. The effect of each marker is adjusted for the subjects' characteristics using a multivariable model. A factor with a p-value of 0.25 or less is incorporated into the multivariable model and a final model is determined by the backward elimination procedure.

A total of 24 adenoma and 80 adenocarcinoma samples are evaluated. A two-sided p-value of 0.05 or less is considered statistically significant. Using the marker CLDN1 as an example, 70% of subjects have 4 or higher pathology score (high group) as listed in Table 6. With a two-sided 5% significance level, a total of 104 samples will provide at least 80% power to detect an odds ratio of 4 when the response rate of a group ranges from 0.2 to 0.6 (Table 8). The statistical power for survival depends upon the event rate, and the event rates of 0.6 to 0.8 are considered for power evaluation. With a two-sided 5% significance level, a total of 104 samples will provide at least 84% power to detect a hazard ratio of 2.25 when the event rate is 0.6 or higher (Table 9). The standard deviation (SD) of the marker is 0.4583 as the proportion of high group is 0.7.

TABLE 9

Statistical Power for Survival (CLDN1 marker).

| HR | Event Rate | SD | Power | HR | Event Rate | SD | Power |
|---|---|---|---|---|---|---|---|
| 2.25 | 0.6 | 0.4583 | 83.5% | 2.5 | 0.6 | 0.4583 | 91.3% |
| 2.25 | 0.7 | 0.4583 | 88.7% | 2.5 | 0.7 | 0.4583 | 94.8% |
| 2.25 | 0.8 | 0.4583 | 92.4% | 2.5 | 0.8 | 0.4583 | 96.9% |

MRI or CT contrast agents are generated with the following properties: acid-stable and protease-resistant for oral delivery; high binding avidity to a cell surface target (e.g. TLR4); sufficient (MR or CT) contrast in vivo when bound; and clearance in stool of unbound CA. An orally available targeted contrast agent cocktail is ultimately developed that can identify suspicious intracolonic lesions using MR or CT

TABLE 8

Statistical Power for Response (CLDN1 marker)

| P0 | Odds Ratio | P1 | Power | Odds Ratio | P1 | Power |
|---|---|---|---|---|---|---|
| 0.2 | 4 | 0.50 | 84.4% | 4.5 | 0.53 | 90.6% |
| 0.3 | 4 | 0.63 | 89.0% | 4.5 | 0.66 | 93.5% |
| 0.4 | 4 | 0.73 | 88.9% | 4.5 | 0.75 | 93.0% |
| 0.5 | 4 | 0.80 | 86.1% | 4.5 | 0.82 | 90.3% |
| 0.6 | 4 | 0.86 | 80.6% | 4.5 | 0.87 | 85.1% |

P0: probability of response in one group,
P1: probability of response in the other group without cathartic bowel prep. Sensitivity and specificity is determined in a cohort of patients undergoing conventional colonoscopy. Compliance for CRC screening increases and more cancers are able to be identified at an early, endoscopically treatable stage. Ligand-based probes conjugated to near infrared fluorescent dye are developed for intravenous delivery to aid in detection of lesions during follow-up fluorescence endoscopy as well as for intraoperative detection during surgical removal of adenocarcinomas.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween.

What is claimed is:

1. A method of detecting colon cancer in a patient comprising:
    obtaining a gastrointestinal tract sample suspected of containing a neoplasm from a patient;
    detecting the presence of at least one biomarker in the sample by contacting the sample with an antibody selected from Table 2 wherein the biomarker is selected from the group consisting of claudin 1 (CLDN1), G protein-coupled receptor (GPR56), glutamate receptor, metabotropic 8 (GRM8), lymphocyte antigen 6 complex, locus G6D (LY6G6D), toll-like receptor 4 (TLR4) and solute carrier organic anion transporter family member 1B3 (SLCO1B3);
    detecting a complex between the antibody and the at least one biomarker;
    generating a pathology score for the at least one biomarker wherein the pathology score is based on staining intensity and degree of epithelial cell positivity; and
    associating the pathology score with presence of colon cancer using statistical methods wherein the pathology score greater than or equal to 4 is indicative of colon cancer.

2. The method of claim 1, wherein the at least one biomarker is a combination of CLDN1, LY6G6D and TLR4.

3. The method of claim 1, wherein the at least one biomarker is a combination of TLR4, GPR56 and CLDN1.

4. The method of claim 1, wherein the at least one biomarker is a combination of TLR4 and GRM8.

5. The method of claim 1, wherein the at least one biomarker is CLDN1.

6. The method of claim 1, wherein the at least one biomarker is TLR4.

7. A method of detecting colon cancer comprising:
    obtaining an expression level of at least one biomarker in a sample by contacting the sample with an antibody selected from Table 2 wherein the biomarker is selected from the group consisting of claudin 1 (CLDN1), G protein-coupled receptor (GPR56), glutamate receptor, metabotropic 8 (GRM8), lymphocyte antigen 6 complex, locus G6D (LY6G6D), toll-like receptor 4 (TLR4) and solute carrier organic anion transporter family member 1B3 (SLCO1B3) in a patient sample;
    detecting a complex between the antibody and the at least one biomarker;
    generating a pathology score for the at least one biomarker based on staining intensity and degree of epithelial cell positivity; and
    comparing the pathology score of the at least one biomarker to a predetermined control pathology score;
    wherein a higher pathology score of the at least one biomarker as compared to the predetermined control pathology score indicates the presence of colon cancer.

8. The method of claim 7, wherein the at least one biomarker is a combination of CLDN1, LY6G6D and TLR4.

9. The method of claim 7, wherein the at least one biomarker is a combination of TLR4, GPR56 and CLDN1.

10. The method of claim 7, wherein the at least one biomarker is a combination of TLR4 and GRM8.

11. The method of claim 7, wherein the at least one biomarker is CLDN1.

12. The method of claim 7, wherein the at least one biomarker is TLR4.

13. A method of screening for colon cancer comprising:
    providing at least one magnetic resonance imaging (MRI) contrast agent wherein the contrast agent is a gadoteric acid (Gd)-sucrose construct;
    binding the at least one contrast agent to at least one colorectal biomarker-specific synthetic ligand wherein the biomarker is selected from the group consisting of claudin 1 (CLDN1), G protein-coupled receptor (GPR56), glutamate receptor, metabotropic 8 (GRM8), lymphocyte antigen 6 complex, locus G6D (LY6G6D), toll-like receptor 4 (TLR4) and solute carrier organic anion transporter family member 1B3 (SLCO1B3);
    adding the contrast agent with bound ligand to a pharmaceutically acceptable carrier to form a composition;
    administering the composition to a patient; and
    imaging the patient using radiation at least about 8.5 hours after administration;

wherein detection of the contrast agent with bound ligand in the patient is indicative of colon cancer.

14. The method of claim 13, wherein multivalent binding is used to bind multiple copies of the biomarker-specific ligand to the contrast agent.

15. The method of claim 13, wherein the at least one biomarker is a combination of CLDN1, LY6G6D and TLR4.

16. The method of claim 13, wherein the at least one biomarker is a combination of TLR4, GPR56 and CLDN1.

17. The method of claim 13, wherein the at least one biomarker is a combination of TLR4 and GRM8.

18. The method of claim 13, wherein the at least one biomarker is CLDN1.

19. The method of claim 13, wherein the at least one biomarker is TLR4.

20. The method of claim 13, wherein the Gd-sucrose construct is comprised of a sucrose scaffold conjugated with a plurality of Gd(III)-DOTA chelates.

21. The method of claim 20, wherein the number of chelates is between about 6 and about 8.

22. A method of screening for colon cancer comprising:
providing at least one acid-stable and protease-resistant computed tomography (CT) contrast agent having a built-in attachment site for a targeting group wherein the contrast agent has a high binding affinity for and is selectively targeted to at least one colorectal cancer lesion;
developing at least one colorectal biomarker-specific synthetic ligand wherein the biomarker is selected from the group consisting of claudin 1 (CLDN1), G protein-coupled receptor (GPR56), glutamate receptor, metabotropic 8 (GRM8), lymphocyte antigen 6 complex, locus G6D (LY6G6D), toll-like receptor 4 (TLR4) and solute carrier organic anion transporter family member 1B3 (SLCO1B3);
binding the at least one contrast agent to the at least one colorectal biomarker-specific synthetic ligand wherein multivalent binding is used to bind multiple copies of the biomarker-specific ligand to the contrast agent;
adding the contrast agent with bound ligand to a pharmaceutically acceptable carrier to form a composition wherein the contrast agent and the bound ligand are stable in the digestive tract;
administering the composition to a patient; and
imaging the patient using radiation at least about 8.5 hours after administration;
wherein detection of the contrast agent with bound ligand in the patient is indicative of colon cancer;
wherein the at least one colorectal biomarker-specific synthetic ligand has a peptidomimetic scaffold.

23. The method of claim 22, wherein the composition is orally administered to the patient.

24. The method of claim 22, wherein the at least one contrast agent is a plurality of gold nanoparticles between about 1.5 nm to about 6 nm in size.

25. The method of claim 22, wherein the at least one biomarker is a combination of CLDN1, LY6G6D and TLR4.

26. The method of claim 22, wherein the at least one biomarker is a combination of TLR4, GPR56 and CLDN1.

27. The method of claim 22, wherein the at least one biomarker is a combination of TLR4 and GRM8.

* * * * *

UNITED STATES PATENT AND TRADEMARK OFFICE
CERTIFICATE OF CORRECTION

PATENT NO. : 9,486,545 B2
APPLICATION NO. : 14/041296
DATED : November 8, 2016
INVENTOR(S) : David L. Morse and Robert J. Gillies It is certified that error appears in the above-identified patent and that said Letters Patent is hereby corrected as shown below:

On the Title Page

Item (72) Inventors should read:
(72) Inventors: David L. Morse, Tampa, FL (US); Robert J. Gillies, Tampa, FL (US); Eugene A. Mash, Tucson, AZ (US)

Signed and Sealed this
Ninth Day of April, 2019

Andrei Iancu
*Director of the United States Patent and Trademark Office*